United States Patent [19]
Krider et al.

[11] Patent Number: 5,985,595
[45] Date of Patent: Nov. 16, 1999

[54] EARLY DETECTION OF BORRELIA INFECTION

[75] Inventors: Hallie M. Krider, Willimantic; Sandra Lee Bushmich, Hebron, both of Conn.

[73] Assignee: The University of Connecticut, Storrs, Conn.

[21] Appl. No.: 08/659,369

[22] Filed: Jun. 6, 1996

Related U.S. Application Data

[63] Continuation-in-part of application No. 08/487,188, Jun. 7, 1995, abandoned.

[51] Int. Cl.$^6$ ........................................................ C12Q 1/04
[52] U.S. Cl. .............................................. 435/34; 435/7.24
[58] Field of Search ................................ 435/4, 7.24, 7.3, 435/29, 34, 40.5, 240.27; 436/172, 811

[56] References Cited

U.S. PATENT DOCUMENTS

| | | | |
|---|---|---|---|
| 4,652,521 | 3/1987 | Confer et al. | 435/34 |
| 4,888,276 | 12/1989 | Shelburne | 435/7 |

OTHER PUBLICATIONS

Benach J., Interactions of Phagocytes with the Lyme Disease Spirochete: Role of the Fc Receptor, J of Infectious Diseases, 150(4) 497–507, Oct. 1984.

Golightly M., The Laboratory Diagnosis of Lyme Borreliosis, Laboratory Medicine 21(5) 299–304, May 1990.

*Primary Examiner*—Ralph Gitomer
*Attorney, Agent, or Firm*—Frommer, Lawrence & Haug LLP; William S. Frommer; Thomas J. Kowalski

[57] ABSTRACT

A method for screening for Lyme borreliosis and other infectious diseases early in the course of the disease are disclosed. It has been found that there is a dramatic difference in surface binding of cultured infectious agents to naturally occurring polymorphonuclear leukocytes (PMNs) (e.g., neutrophils) between infected and noninfected animals, which may be present early in the course of the disease, before measurable antibody response. This binding response can be rapidly and accurately distinguished and quantitated using various detection techniques. The method involves visualizing the surface binding of the cultured infectious agent to naturally-occurring PMN to detect the infection.

17 Claims, 16 Drawing Sheets

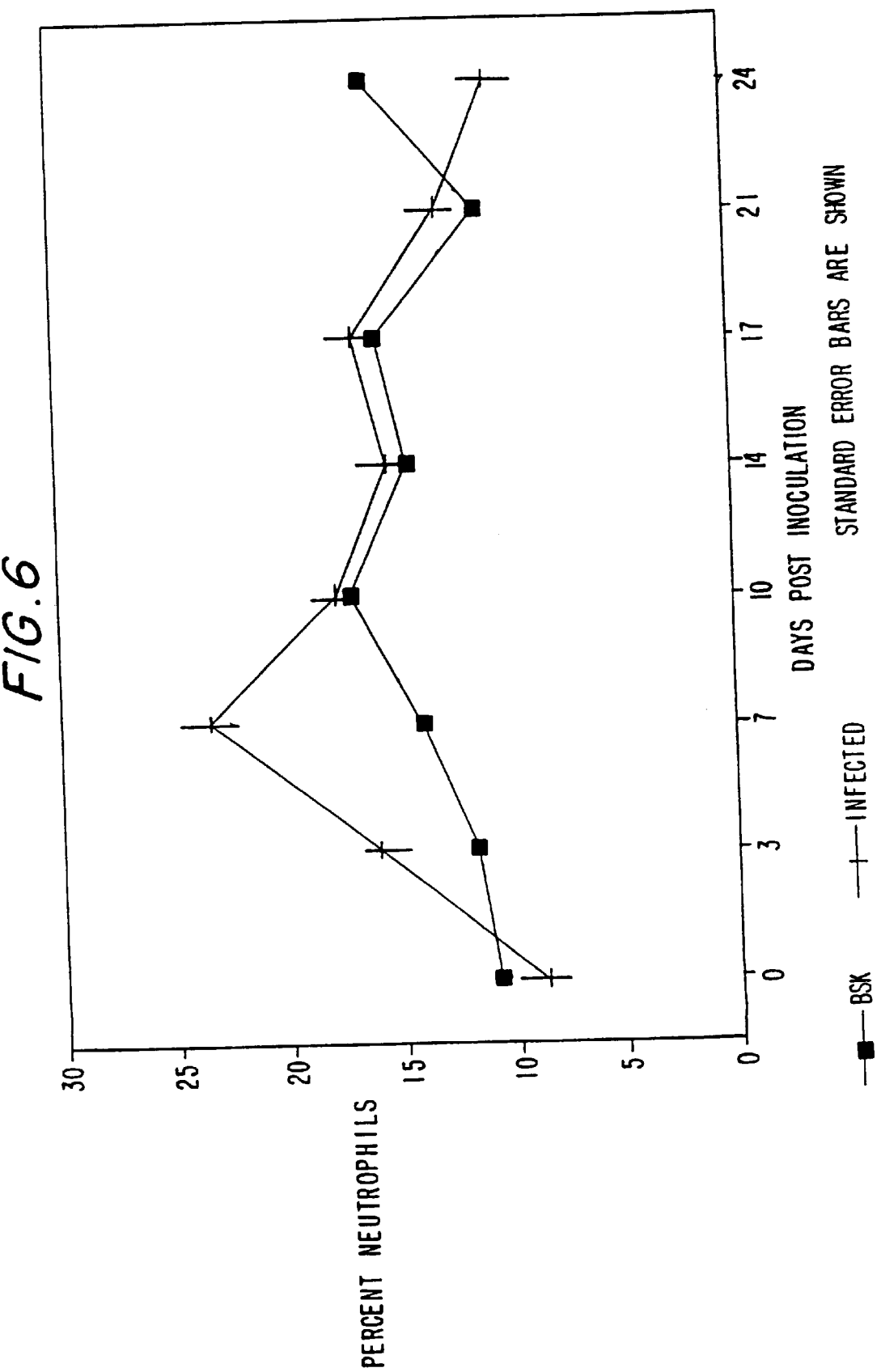

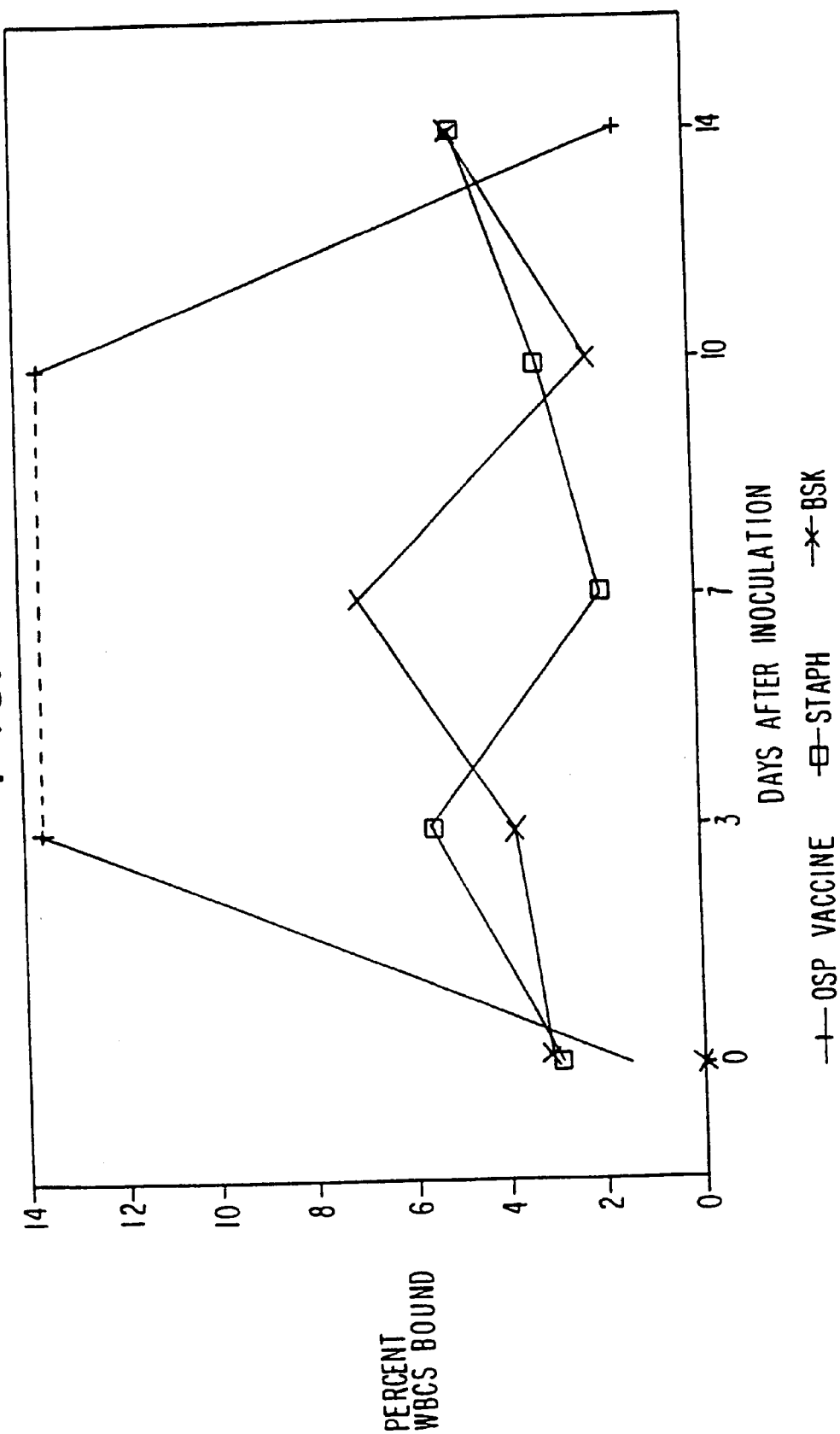

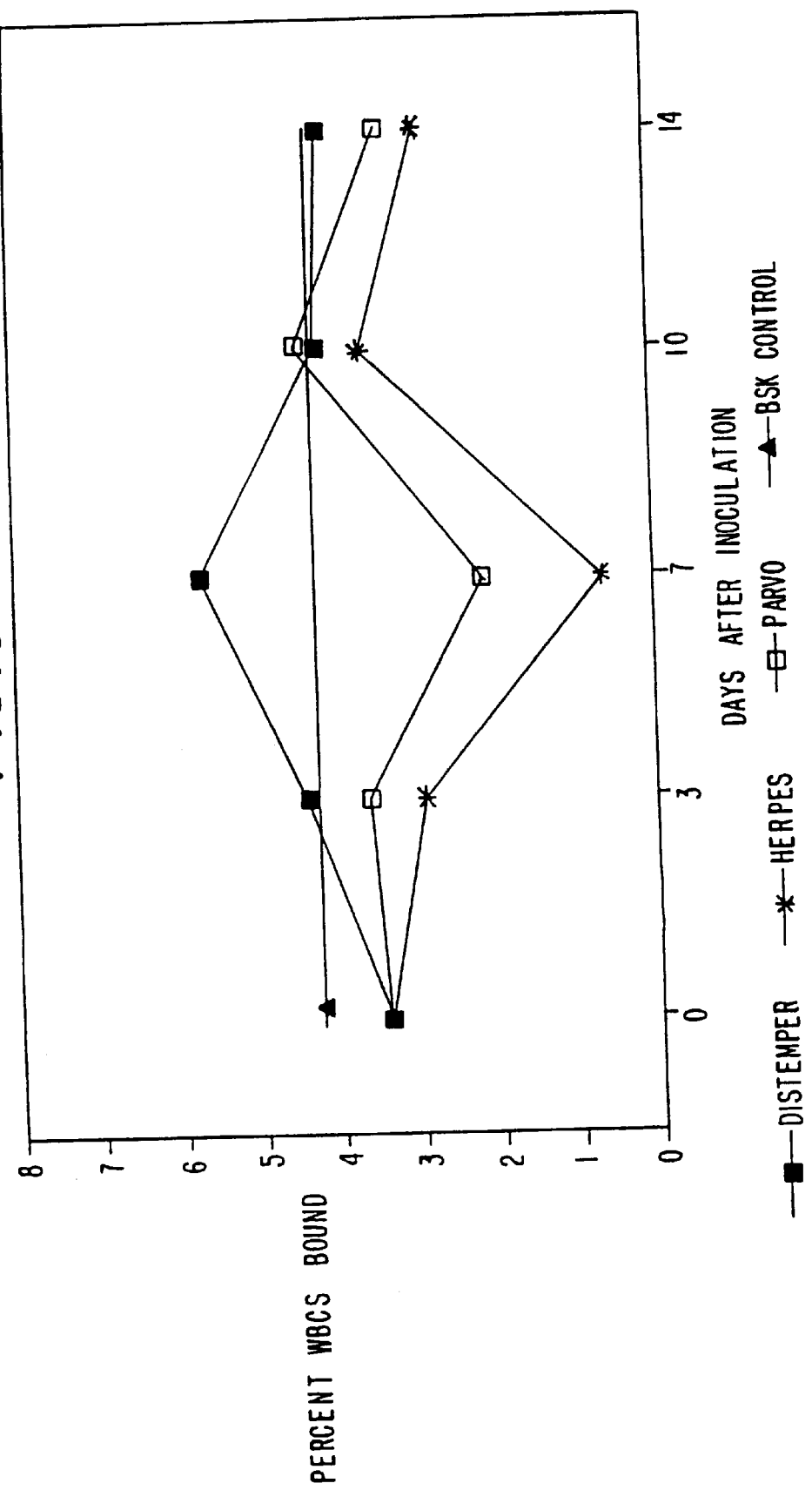

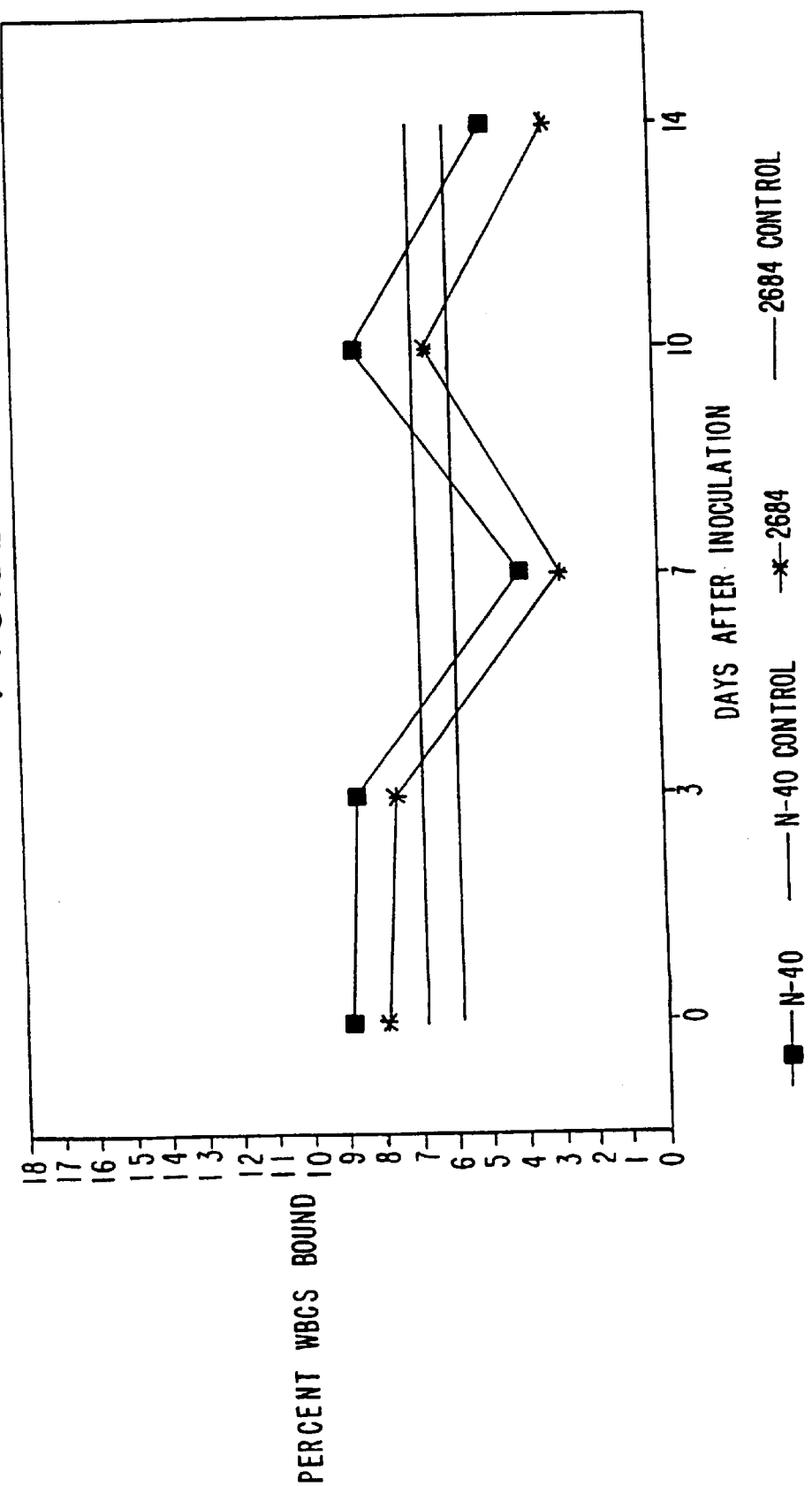

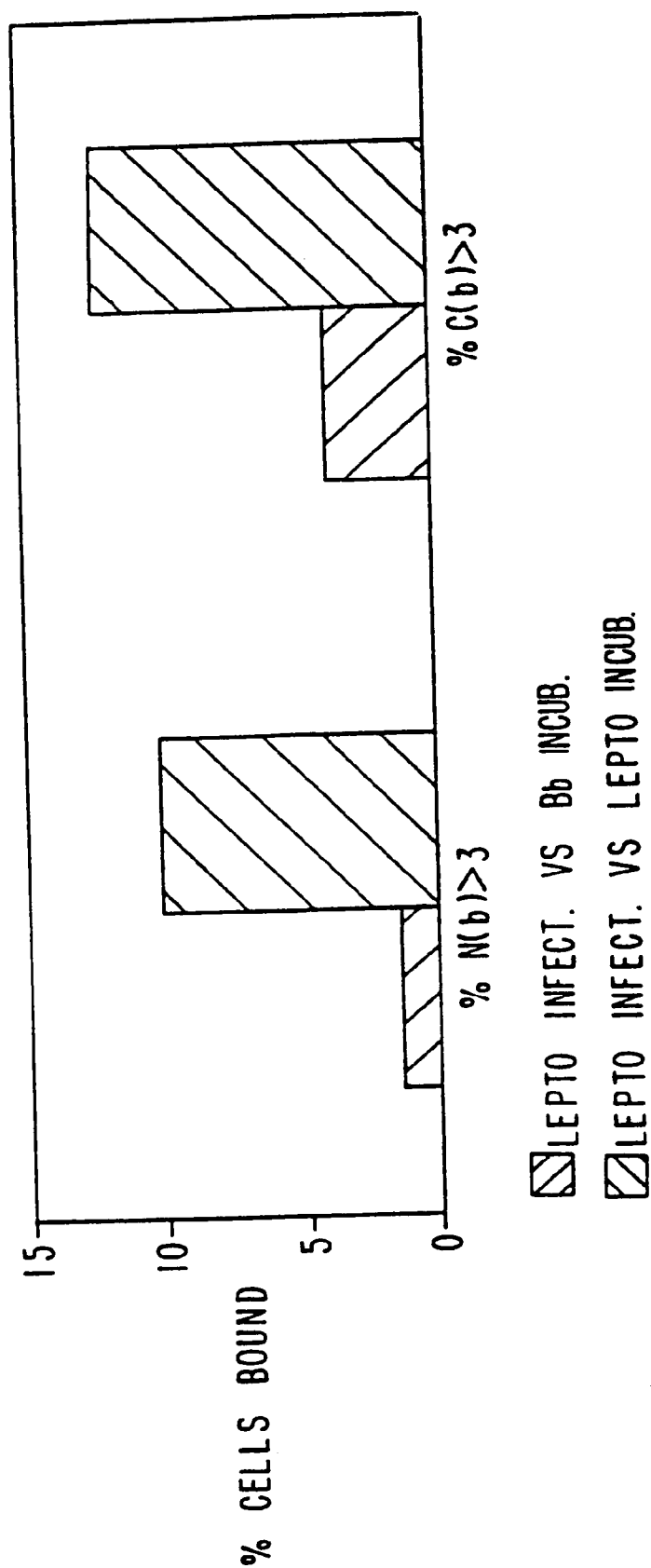

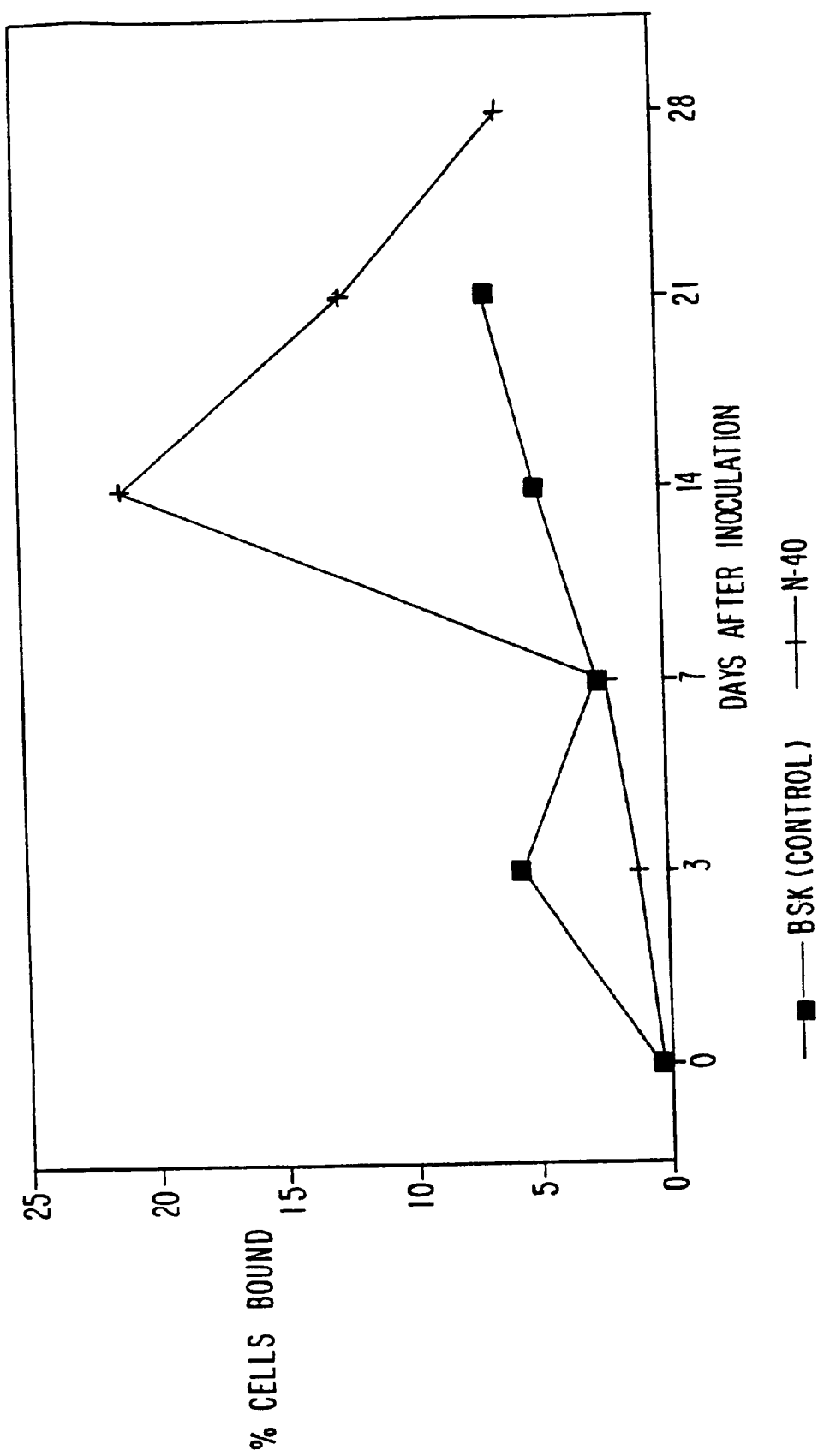

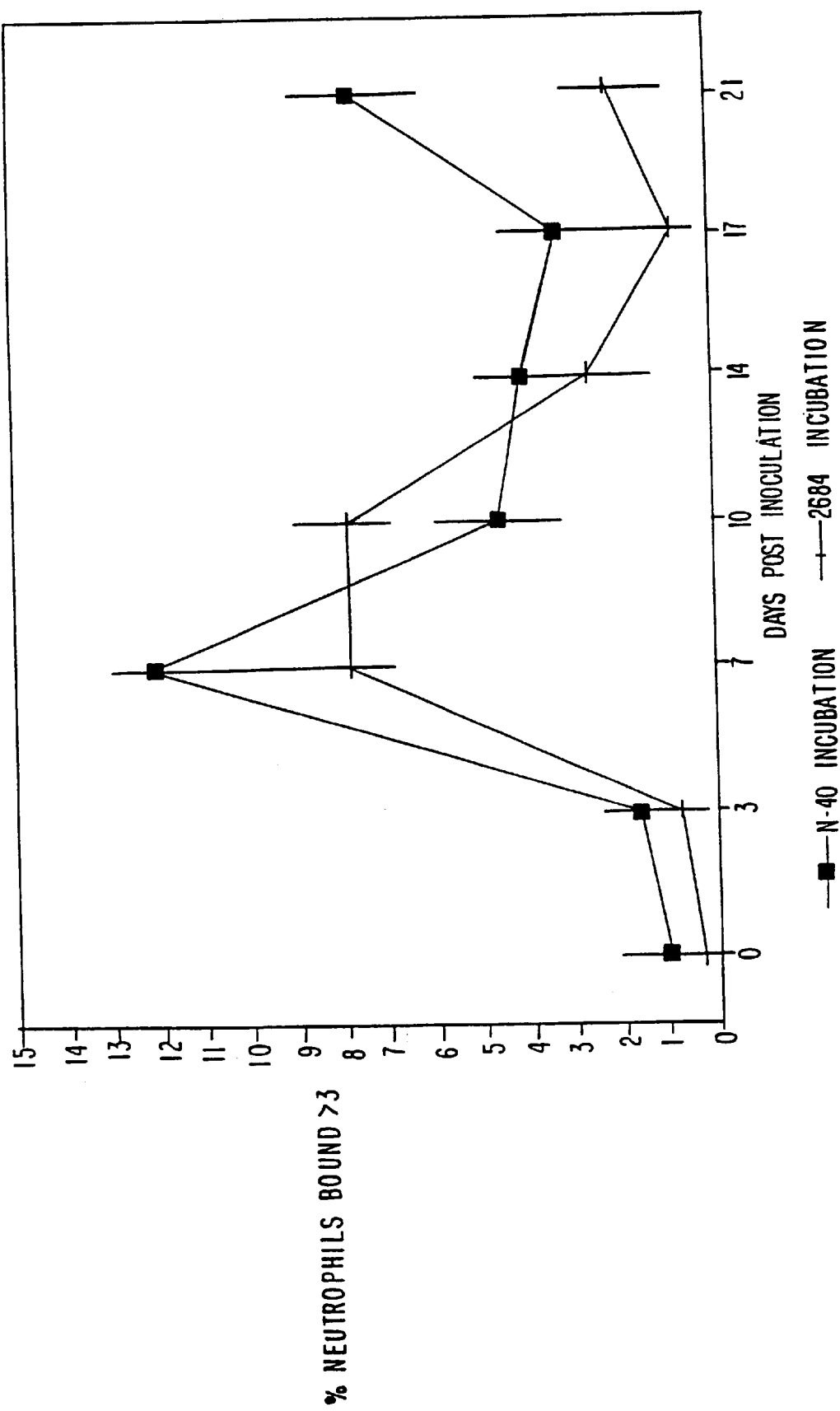

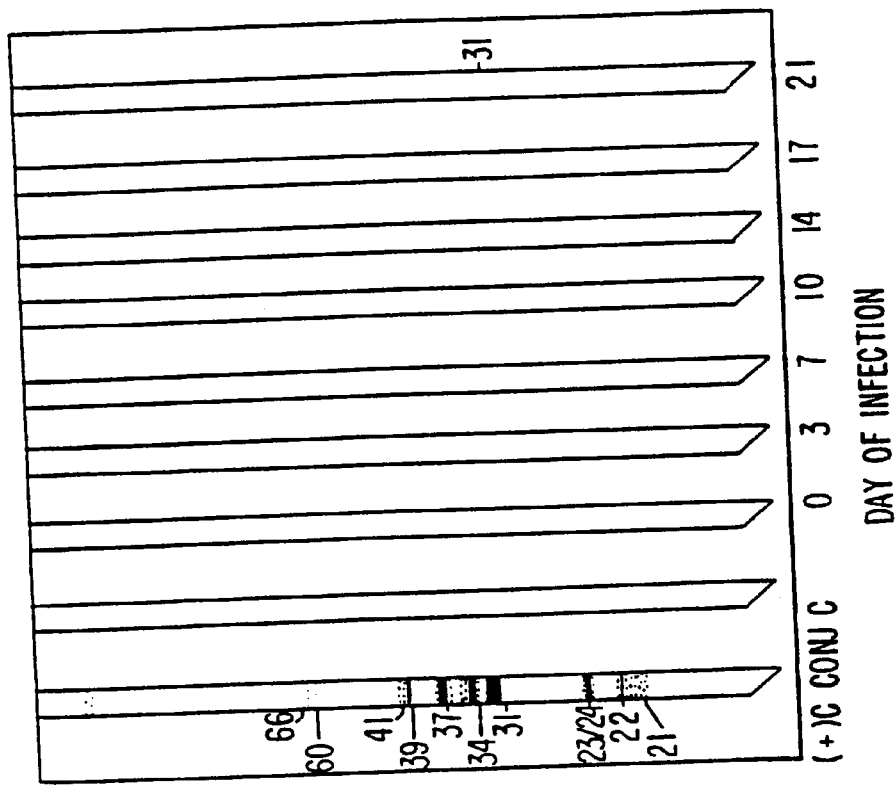

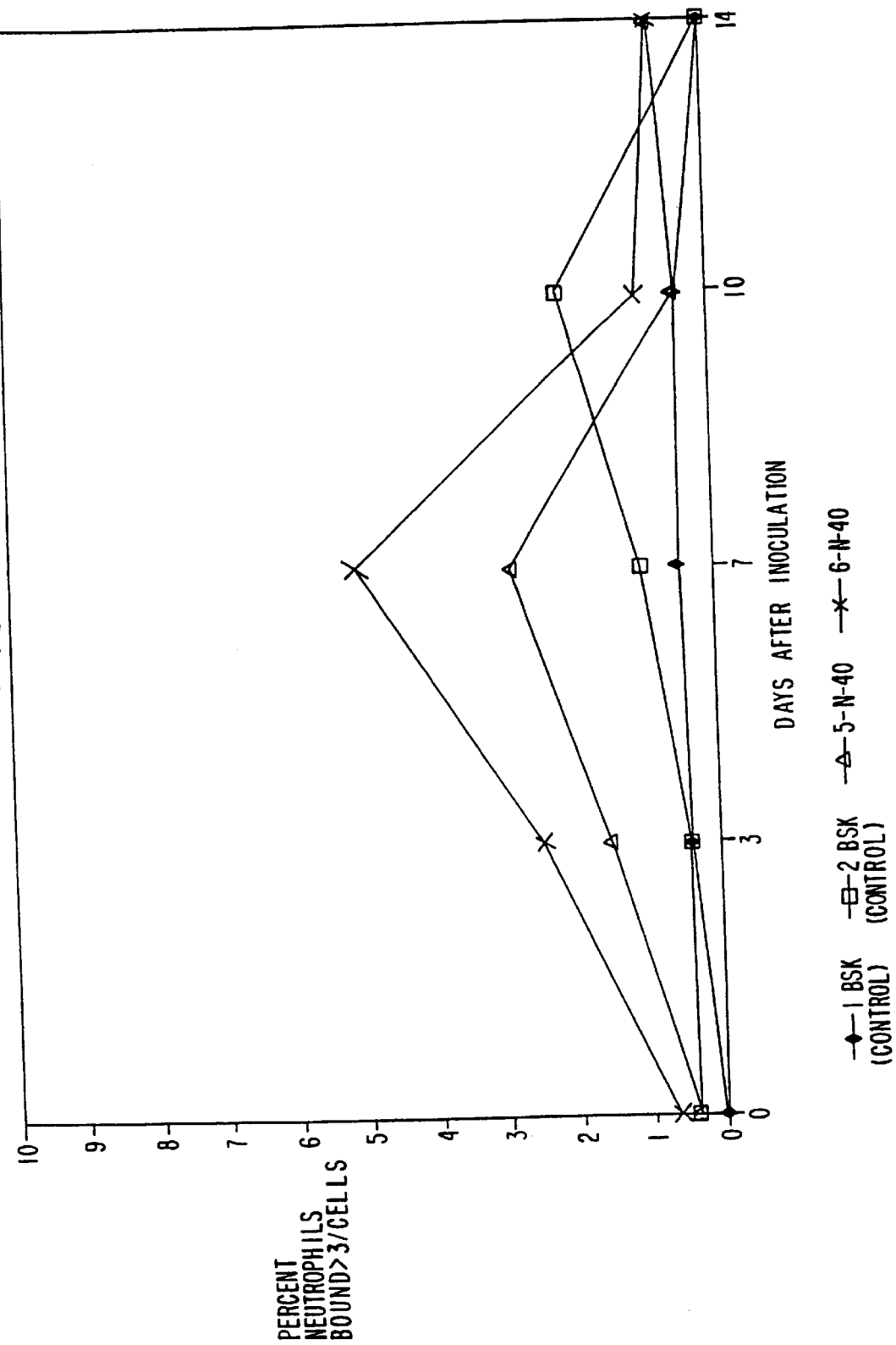

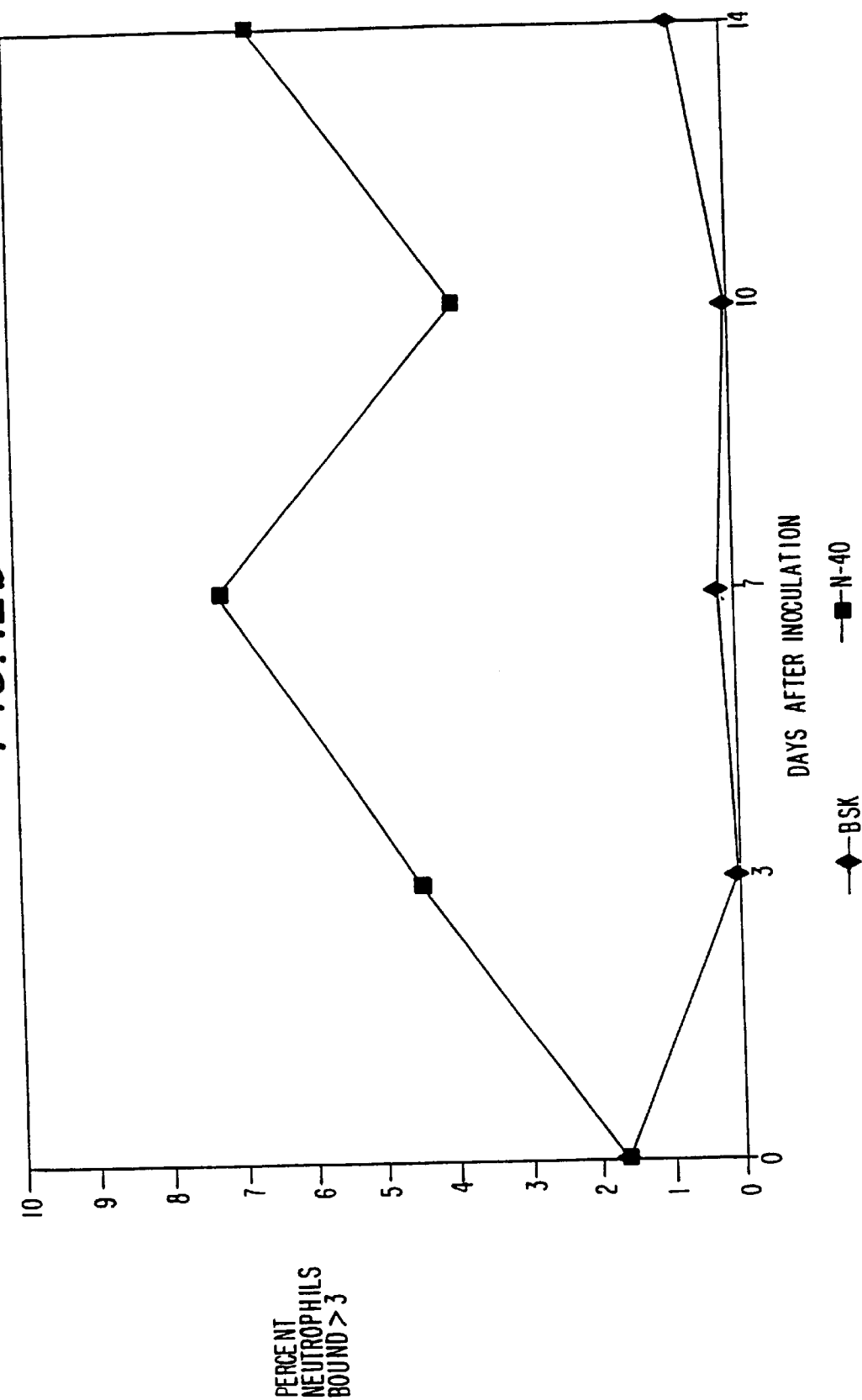

EARLY DETECTION OF BORRELIA INFECTION

CROSS REFERENCE TO RELATED APPLICATIONS

This application is a continuation-in-part of application Ser. No. 08/487,188, filed Jun. 7, 1995 now abandoned.

Reference, especially with respect to amino acid sequences and nucleic acid sequences therefor of *Borrelia burgdorferi*, such as OspA, is made to each of applications Ser. No. 08/079,601, filed Jun. 23, 1993; U.S. Pat. No. 5,582,990; Ser. No. 08/375,993, filed Jan. 20, 1995; Ser. No. 08/137,175, filed Oct. 26, 1993; Ser. No. 08/262,220, filed Jun. 20, 1994; Ser. No. 07/422,881, filed Oct. 18, 1989; to WO 90/04411 (Symbicom AB).

Reference, especially with respect to recombinant Borrelia proteins, the expression thereof by vectors, and nucleic acid sequences therefor, is also made to each of applications Ser. No. 07/973,338, filed Oct. 29, 1992; Ser. No. 08/373, 455 (Rule 62 continuation of Ser. No. 07/973,338), filed Jan. 17, 1995; Ser. No. 08/211,891, filed Oct. 16, 1992 (national phase of PCT/US92/08697); Ser. No. 07/888,765, filed May 27, 1992; and Ser. No. 07/779,048, filed Oct. 18, 1991.

FIELD OF THE INVENTION

The present invention relates to diagnostic tests and more particularly to a method for the rapid and reliable detection of the presence of pathogens or other foreign substances in a human or animal. A list of references which more fully describe the state-of-the-art to which this invention pertains as well as certain aspects of the invention itself can be found at the end of the specification immediately preceding the claims. The contents of these references and all documents cited herein are hereby incorporated by reference into the present disclosure.

BACKGROUND OF THE INVENTION

Lyme borreliosis is the most prevalent tick-borne disease in the United States as well as one of the most important tick-borne infectious diseases worldwide. It is endemic in much of the northeastern United States, Minnesota, Wis., and parts of the Pacific Northwest. The bacterial spirochete *Borrelia burgdorferi* is the causative agent for Lyme disease. Infection with *B. burgdorferi* produces local and systemic manifestations. Local symptoms that appear early after infection include a skin lesion at the site of the tick bite, termed erythema chronicum migrans (ECM), as well as fever and flu-like illness. Weeks to months after infection, systemic manifestations that include rheumatic, cardiac and neurological symptoms appear. The early local phase of *B. burgdorferi* infection is easily treatable with antibiotics. However, the later systemic phases have proved to be more refractory to antibiotics.

Much attention has been given to investigation of the immune response to *B. burgdorferi* infection in animal and human model systems, and how the initial phagocytic and subsequent humoral and cellular responses affect the pathogenesis of the disease. The success of initial phagocytic interactions with invading spirochetes quite probably influences the progression of disease, and thus has been the subject of much investigation.

There are numerous observations suggesting a cell-based response to infection. Several studies have demonstrated that neutrophils and monocytes bind and phagocytose both opsonised and non-opsonised *B. burgdorferi* of high and low passage strains. See, e.g. Peterson et al., *Infect. Immun.* (1984) 46:608–611. Opsonization of the spirochetes with specific immune serum greatly enhanced phagocytosis; this effect appears to be dependent on the availability of polymorphonuclear Fc receptors, and independent of heat dependent serum factors. Treatment of the spirochetes with normal serum [Benach et al., *J. Infect. Dis.* (1984) 150:497–507] or normal whole blood [Banfi et al., *J. Applied Bact.* (1989) 67:37–45] (non-specific opsonization) resulted in a phagocytosis rate intermediate between non-opsonized and immune serum opsonized treatments. Phagocytic cells are observed in the infiltrates of experimentally induced skin lesions in animal models and humans, as reported by Benach et al., *Yale J. Biol. Med.* (1984) 57:599–605. It is speculated that the cells participating in immediate responses may differ from those circulating at later times in the infective cycle. In addition, it has been shown that while natural killer (NK) cells numerically increase shortly after infection, the NK cell activity of infected individuals is depressed. This may be related to early expression of suppressor cell activity. Cellular response begins early and prior to a measurable humoral response.

For optimum effectiveness, antibiotic treatment of Lyme borreliosis should be administered early in the course of the disease, when spirochetemia and the polymorphonuclear leukocyte (PMN) phagocytic responses are prominent. Early, appropriate treatment aborts progression to more severe cardiac neurological and arthritic manifestations in the majority of cases. In addition to maximizing the cure rate and minimizing patient suffering, early treatment is more cost effective than less successful treatments for later arthritic and neurological manifestations of Lyme disease, which may include extended periods of intravenous antibiotic therapy. Thus, early diagnosis of Lyme disease is essential.

Lyme disease is currently difficult to definitively diagnose. The early symptoms are often non-specific. Further, although *B. burgdorferi*-infected Ixodid ticks are the predominant source of infection, some patients have no history of a tick bite and 25–30% of the patients do not develop ECM. A screening test which reliably detects *B. burgdorferi* infection early in the course of the disease would allow early diagnosis and treatment, and eliminate the need for the physician to treat patients based on clinical suspicion alone.

Currently available diagnostic tests, however, are inadequate. Although *B. burgdorferi* spirochetes have been demonstrated in the blood, urine, cerebrospinal fluid (CSF) and synovial fluid of infected animals and humans, their numbers are too few, and their presence too variable, to allow reliable diagnosis by traditional dark field examination. Culture of these organisms from body fluids is difficult due to the low number of spirochetes in samples and the slow growth rate of wild strain *B. burgdorferi* in culture; the process can take up to five weeks. Bacterial contamination of samples is another common difficulty, as the rich Barbour-Stoenner-Kelly (BSK) media needed to support *B. burgdorferi* growth will also encourage growth of contaminants, and the few antibiotics that can be used to decrease contamination also slow *B. burgdorferi* growth considerably.

The most commonly used diagnostic tests for Lyme disease, Enzyme Linked Immunosorbent Assay (ELISA) and Immune Fluorescent Antibody (IFA) techniques, measure antibodies to *B. burgdorferi*. These tests are often inaccurate, for several reasons. Clinical symptoms of Lyme disease often develop prior to the development of measurable antibody response. It may take as long as three to six weeks after infection for measurable IgM to develop, and months for IgG to reach measurable levels, while clinical signs may occur within two to twenty days following infection. In addition, certain individuals may not mount a measurable antibody response, development of antibody titer may be muted by early antibiotic treatment, and the sensitivity of antibody tests, especially IFA, varies widely among laboratories. The use of different *B. burgdorferi* strains as antigens leads to varied test results in ELISA. Finally, there may be some lack of specificity in serological testing of patients with other spirochetal (e.g. Leptospira or Treponema) or other borrelial diseases (e.g. *Borrelia hermseii*). As a result, syphilitic patients, using current diagnostic tests, may test falsely positive for Lyme Disease, and Lyme Disease patients may test falsely positive for syphilis. This is problematic due to the different treatments involved for each of these diseases as well as the social stigma attached to syphilis as a sexually transmitted disease.

Thus there remains a need for a diagnostic test which reliably detects *B. burgdorferi* infection in all individuals early in the course of the disease.

There are many other diseases for which a diagnostic test for use in the early stages of the disease is desirable or necessary, because the disease becomes difficult to treat, or fatal, before direct evidence of the identity of the pathogen can be found, or before the patient seroconverts.

For example, acute bacterial meningitis, particularly meningococcal meningitis (caused by *Neisseria meningitidis*), can be lethal within hours, with the patient rapidly progressing from symptoms such as sore throat, fever, headache, stiff neck and vomiting to drowsiness, stupor, coma and death. The use of antibiotics has reduced the fatality rate of acute bacterial meningitis to less than 10% in cases recognized early, but when diagnosed late it is often fatal. Current methods of diagnosis include a lumbar puncture followed by culturing and examination of the cerebrospinal fluid (CSF) for the presence of bacteria. However, such a test is time consuming, and lumbar puncture can cause neurological damage in the presence of a brain abscess or other mass lesion. In addition, if no bacteria are found in the culture it is difficult to determine whether viral meningitis or bacterial meningitis is the diagnosis, and therefore how to treat the patient. Due to the rapid progress of the disease, when bacterial meningitis is seriously suspected, administration of antibiotics must begin before the results of such diagnostic tests.

Similarly, septicemia (invasion of the circulation by pathogenic bacteria and their toxins) can result in septic shock, characterized by acute circulatory failure and multiple organ failure including the kidneys, lungs and heart. Mortality ranges from 25–90%, and is higher when treatment is not begun soon enough. Therefore, administration of antibiotics should begin before the results of blood cultures are known. This means treatment must be selected based on the physician's educated guess, and unnecessary agents may be administered. Further, culture results may be negative, especially in patients who have had prior antibiotic therapy, but a negative culture does not exclude septicemia.

Gonorrhea, a sexually transmitted infection caused by the bacterium *Neisseria gonorrhoeae*, can lead to complications such as bacteremia and gonococcal arthritis if left untreated. However, it is a disease for which there is no rapid nonculture diagnostic test. A urethral Gram stain allows identification of the causative organism in about 90% of men, but a cervical Gram stain is only about 60% sensitive in women. Nor is there a reliable serologic diagnostic test for gonorrhea currently available.

Syphilis is caused by the spirochete bacterium *Treponema pallidum*. There are currently two types of serological tests used to diagnose this sexually transmitted disease: nonspecific screening tests which detect a substance called syphilitic reagin, and specific tests which detect antitreponemal antibodies. The screening tests are easy to perform and inexpensive, but have a high rate of false positives and do not become positive until three to six weeks after the initial infection. The treponemal tests are more accurate, but do not become positive until three to four weeks after infection. An immediate diagnosis of syphilis can be made by demonstrating *T. pallidum* in fluid from lesions by darkfield microscopy, but skill is needed to collect and correctly identify the organism.

SUMMARY OF THE INVENTION

It has now surprisingly been found that there is a dramatic qualitative and quantitative difference in surface binding and phagocytosis of cultured *B. burgdorferi* to naturally-occurring PMN (e.g., neutrophils) between heparinized whole blood of infected and noninfected animals, which may be present early in the course of the disease, before measurable antibody response. This binding response can be rapidly and accurately distinguished and quantitated using various imaging techniques. This finding has been used to develop a rapid, inexpensive method for screening for early Lyme borreliosis. Moreover, this finding has led to the discovery that this difference occurs distinctly and specifically as to foreign substances other than *B. burgdorferi*, thereby providing a rapid, inexpensive method for screening for exposure to virtually any pathogen, e.g., bacteria, viruses, yeast or certain drugs.

Accordingly, the present invention provides a method for detecting exposure to a foreign substance in a human or animal, comprising the steps of obtaining a tissue or fluid sample from the animal or human which contains polymorphonuclear leukocytes. The sample is contacted with the foreign substance of interest. The fluid or tissue is labelled with one or more labels which allow detection of the white blood cells and of the foreign substance (e.g. a DNA fluorochrome) either before, during or after contacting the sample with the foreign substance. An appropriate method (e.g., fluorescence microscopy) is then utilized to observe the degree of binding of the foreign substance to the white blood cells. The degree of binding can indicate exposure to, or the presence of, the foreign substance, especially when compared to a control.

In a preferred embodiment, the leukocytes are neutrophils. The neutrophils can be from any fluid or tissue from an animal or human. The foreign substance can be any pathogen, e.g. bacteria, viruses, yeasts, fungi, protozoans, parasitic animals, or biological molecules including a protein, lipoprotein (e.g., in a particularly preferred embodiment, OspA or OspC of *B. burgdorferi*), a lipopolysaccharide or a glycoprotein.

In another preferred embodiment, the foreign substance is a bacteria selected from the group consisting of Borrelia spp., *E. coli, Bordetella pertussis*, Neisseria spp., Staphylococcus spp., Leptospira spp., Treponema spp., Listeria spp. and Mycoplasma spp.

In a further preferred embodiment, the foreign substance is a virus selected from the group consisting of parvoviruses, herpesviruses, canine distemper virus, papovavirus and parainfluenza viruses.

In still a further preferred embodiment, the fluid or tissue obtained from the human or animal is selected from the group consisting of blood, respiratory secretions, urine, cerebrospinal fluid, exudate from skin lesions or abscesses, exudate from the lacrimal sac, and synovial fluid.

The method thus provides a reliable way to ascertain whether an animal or human has been exposed to the foreign substance, for instance whether the animal or human has been infected by, inoculated with or otherwise exposed to an antigen, immunogen or pathogen. Thus, one can reliably ascertain whether an animal or human has been infected, inoculated or otherwise exposed to the foreign substance.

These and other advantages and embodiments are disclosed in or are obvious from the following description.

BRIEF DESCRIPTION OF DRAWINGS

In the following detailed description, reference is made to the accompanying drawings wherein:

FIG. 6 is a graphical representation of the percentage of neutrophils out of total white blood cells in the blood of mice infected with B. burgdorferi versus the percentage of neutrophils out of total white blood cells in the blood of mice injected with BSK medium;

FIG. 7 is a graphical representation of the percentage of white blood cells from mice injected with BSK medium binding B. burgdorferi spirochetes of strain N-40; the percentage of white blood cells from mice injected with Staphylococcus spp. binding B. burgdorferi spirochetes of strain N-40; and the percentage of white blood cells from mice injected with OspA vaccine binding B. burgdorferi spirochetes of strain N-40;

FIGS. 8a and 8b are graphical representations of the percentage of white blood cells from mice injected with distemper, herpes, parvo and influenza pathogens binding B. burgdorferi spirochetes of strain N-40;

FIG. 9 is a graphical representation of the comparison of Leptospira and B. burgdorferi binding in white blood cells of Leptospira infected mice;

FIG. 10 is a graphical representation of the percentage of cells bound to B. burgdorferi spirochetes of strain N-40 in male mice inoculated with the N-40 strain;

FIG. 11a is a graphical representation of the percentage of neutrophils bound to B. burgdorferi spirochetes of strain N-40 in mice intradermally inoculated with B. burgdorferi;

FIG. 11b shows an immunoblot analysis of mice infected intradermally with B. burgdorferi spirochetes of strain N-40;

FIGS. 12a and 12b are graphical representations of the percentage neutrophils bound in mice serially bled by retroorbital bleeding (FIG. 12a) or serially killed by guillitine bleeding (FIG. 12b) in mice infected with B. burgdorferi spirochetes of strain N-40.

DETAILED DESCRIPTION OF THE INVENTION

Figure 1:
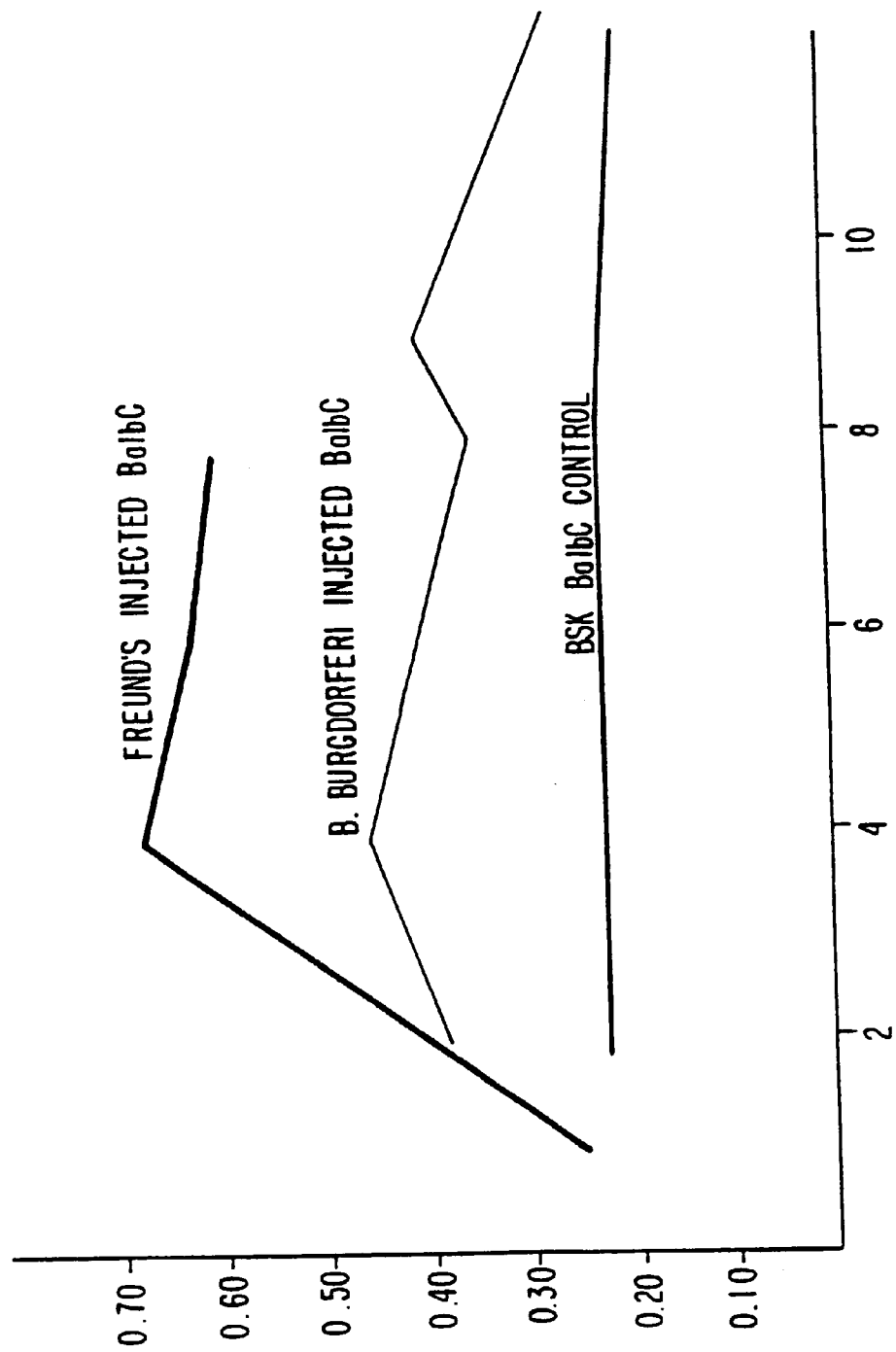
FIG. 1 is a graphical representation of the percentage of neutrophils out of total white blood cells in blood from Balb/C mice injected with B. burgdorferi; Balb/C mice injected with Freund's adjuvant; and a control group of Balb/C mice injected only with BSK medium.

As noted above, the present invention is concerned with a method for the rapid and reliable detection of the presence of pathogens or other foreign substances in a human or animal.

Neutrophils are a type of polymorphnuclear leukocyte (PMN), whose primary known functions are phagocytosis (the ingestion and destruction of particulate material) and the release of chemicals involved in inflammation. They comprise approximately 50–70% of total leukocytes (white blood cells) in normal human blood. It has been found that when whole blood of seropositive animals is mixed with cultured B. burgdorferi, neutrophils bind large numbers of the spirochetes. This response has been observed in canine, equine, bovine, caprine and murine blood. The blood smears can be stained, using stains such as DAPI, Hoechst (e.g., Hoechst 33258), acridines (e.g., Acridine Orange) and other fluorescent DNA stains to visualize the binding. Antibodies linked to fluorochromes or colorigenic agents, such as fluorescein isothiocyanate (FITC), rhodamines, Texas Reds, and the like, are also suitable. Because the binding involves white blood cells, particularly neutrophils, the method of the claimed invention is not limited to the use of whole blood but can involve the examination of smears of any body fluid or tissue where white blood cells are likely to be found, e.g. urine, respiratory secretions, CSF, the exudate from skin lesions or abscesses, exudate from the lacrimal sac, synovial fluid, and the like.

The origin of the specificity of the binding response, and the origin of the cells that bind, is not yet known. The increase in the number of neutrophils which bind spirochetes is matched by only a slight increase in the total number or fraction of the cells which are neutrophils. That is, neutrophilia is not a necessary component of the syndrome associated with a host response to early Lyme disease. Thus, the cells could be recruiting recognition and/or binding factors from some other source. Also, the rise in the number of competent cells may not result from new cells produced in response to infection.

The material is spread on slides, air dried, fixed, stained and examined using a microscope. The presence and degree of cell binding is then observed by indirect techniques. In a preferred embodiment, the protocol for a simple hematocrit test is altered to include the mixing of reagents prior to centrifuging the blood. Enzymatic or fluorescent tags would show if there is cell binding, and would allow a quantitative evaluation. In another prefered embodiment, enzymes may be attached in order to generate a calorimetric reaction that could be read in the serum, or a precipitated product that would appear at the layer of the cells. A sophisticated reader of this type exists as the QBC instrument marketed by Becton Dickinson. Flow cytometry, e.g., fluorescent cell sorting utilizing a fluorescence-activated cell sorter (FACS) machine is useful with the claimed method. Film readers and other approaches may also be used with the claimed method. The use of fluroescent or enzyme-linked tags to provide the qualitative and quantitative markers for the test has the advantage of allowing a positive internal control and standard to be incorporated into the test. That is, antibodies which will bind other cellular components to ensure that the reagents are still active, the blood is properly preserved, mixing was complete, etc., can be added.

In preliminary experiments, Balb/C mice were innoculated with *B. burgdorferi*, Freund's adjuvant or control BSK media. The mice were bled three times weekly for two weeks following infection. The whole blood was mixed with cultured *B. burgdorferi* spirochetes. Thin blood smears were prepared and stained with a DNA fluorochrome to visualize white blood cell nuclei and the *B. burgdorferi* spirochetes.

Figure 2:
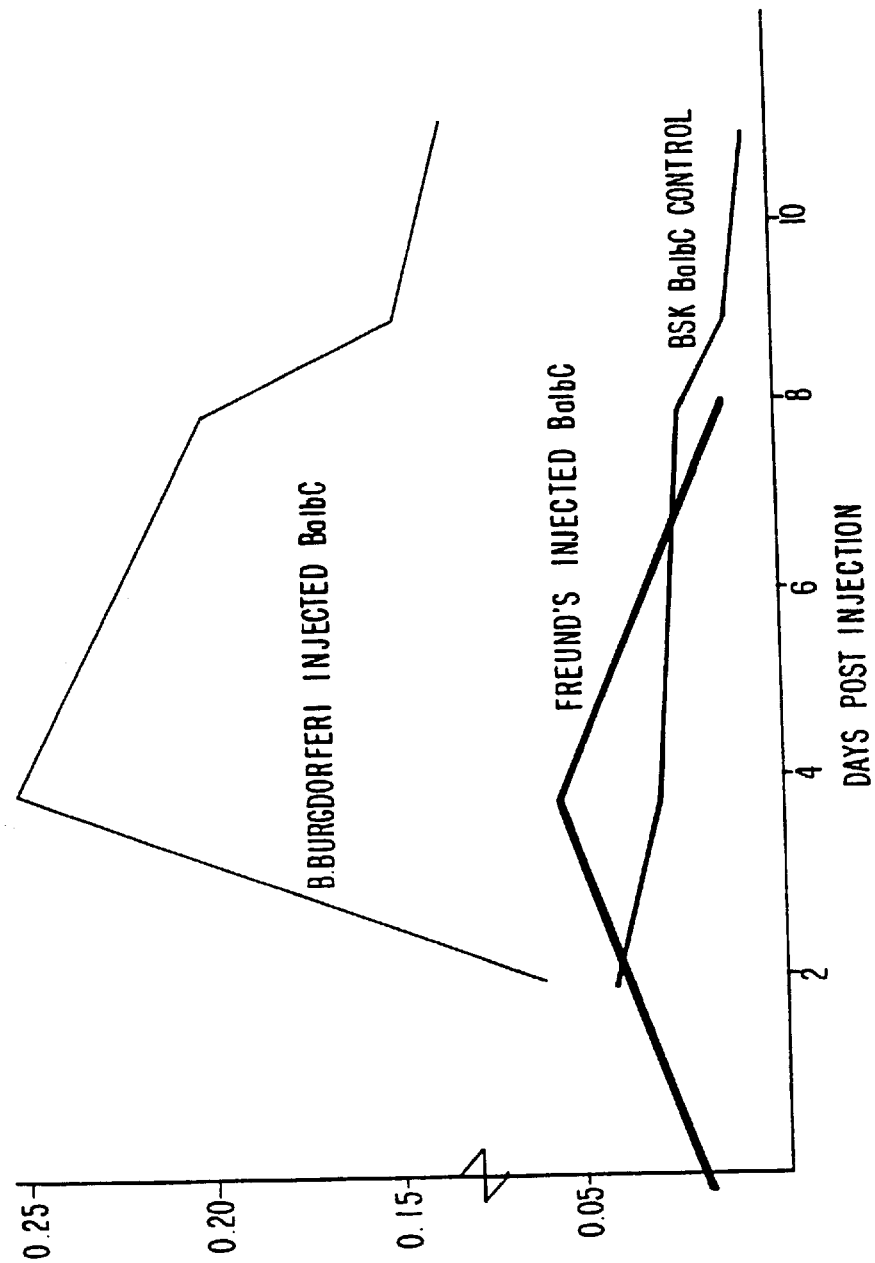
FIG. 2 is a graphical representation of the percentage of white blood cells binding B. burgdorferi spirochetes out of total white blood cells in blood from Balb/C mice injected with B. burgdorferi; Balb/C mice injected with Freund's adjuvant; and a control group of Balb/C mice injected only with BSK medium.

The results, shown in FIG. 2, showed an increase in *B. burgdorferi* binding to neutrophils in the blood from *B. burgdorferi*-infected mice compared to mice innoculated with Freund's adjuvant and the control mice. The binding response was detectable as early as day 2–4 post infection (preceding measurable antibody response in mice by approximately one week). These results suggested that the binding response was specific, and occurred very early.

There are both quantitative and qualitative differences which characterize the background binding observed in the control in these experiments. Most of the background binding, which was at or below 5%, is the result of platelets associating with the spirochetes, followed by macrophage scavenging of the debris. Phase constrast microscopy allows the platelets to be seen clearly, and it has been shown that the background can be reduced by adding fewer spirochetes to the test media. Background binding can be greatly reduced by any approach (e.g., use of the QBC instrument) that physically separates platelets and associated debris from whole cells.

Figure 3:
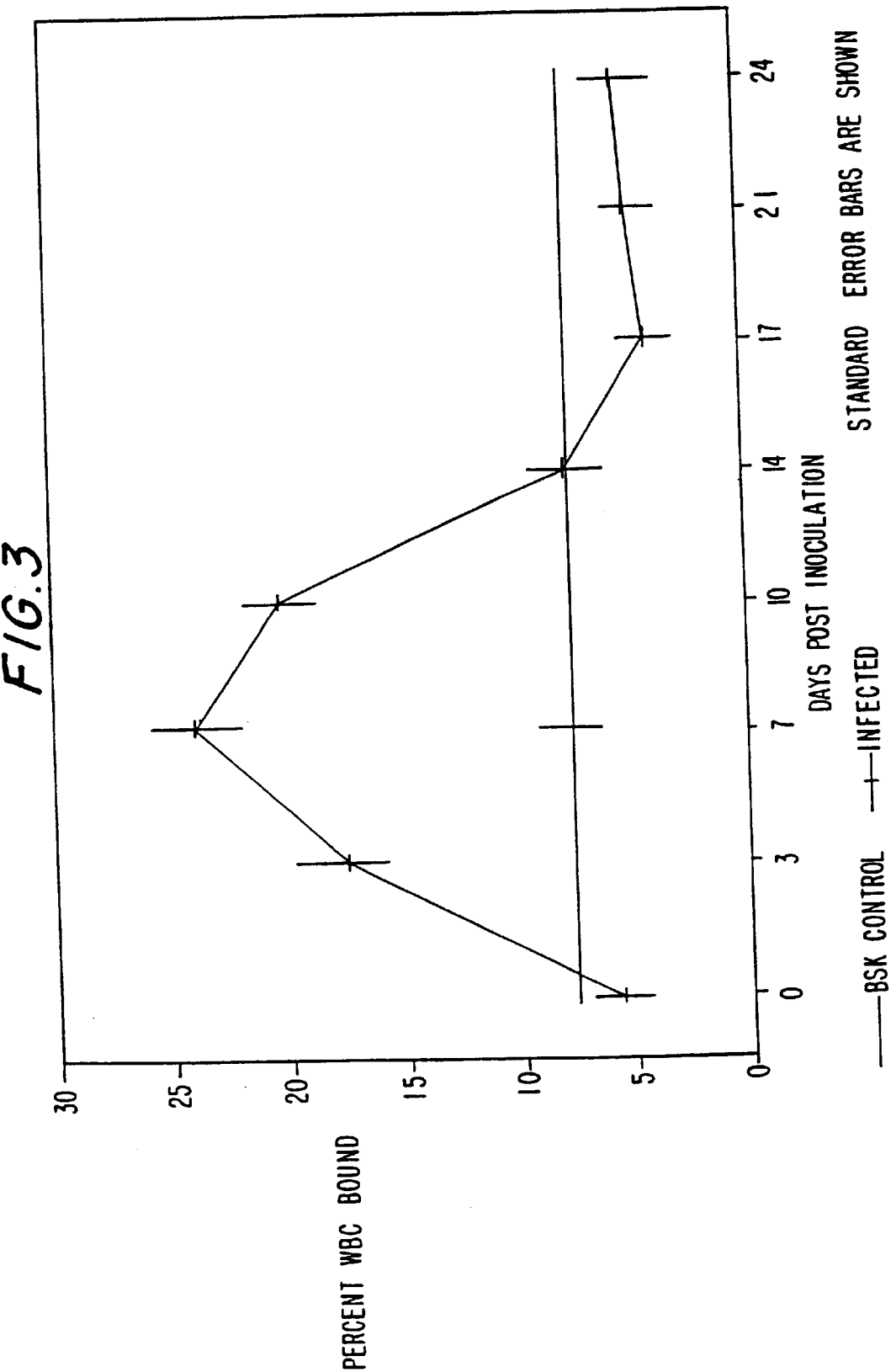
FIG. 3 is a graphical representation of the percentage of white blood cells from mice injected with one of strains N-40, 2684 or 25550 of B.burgdorferi binding B. burgdorferi spirochetes of strain N-40.
Figure 4:
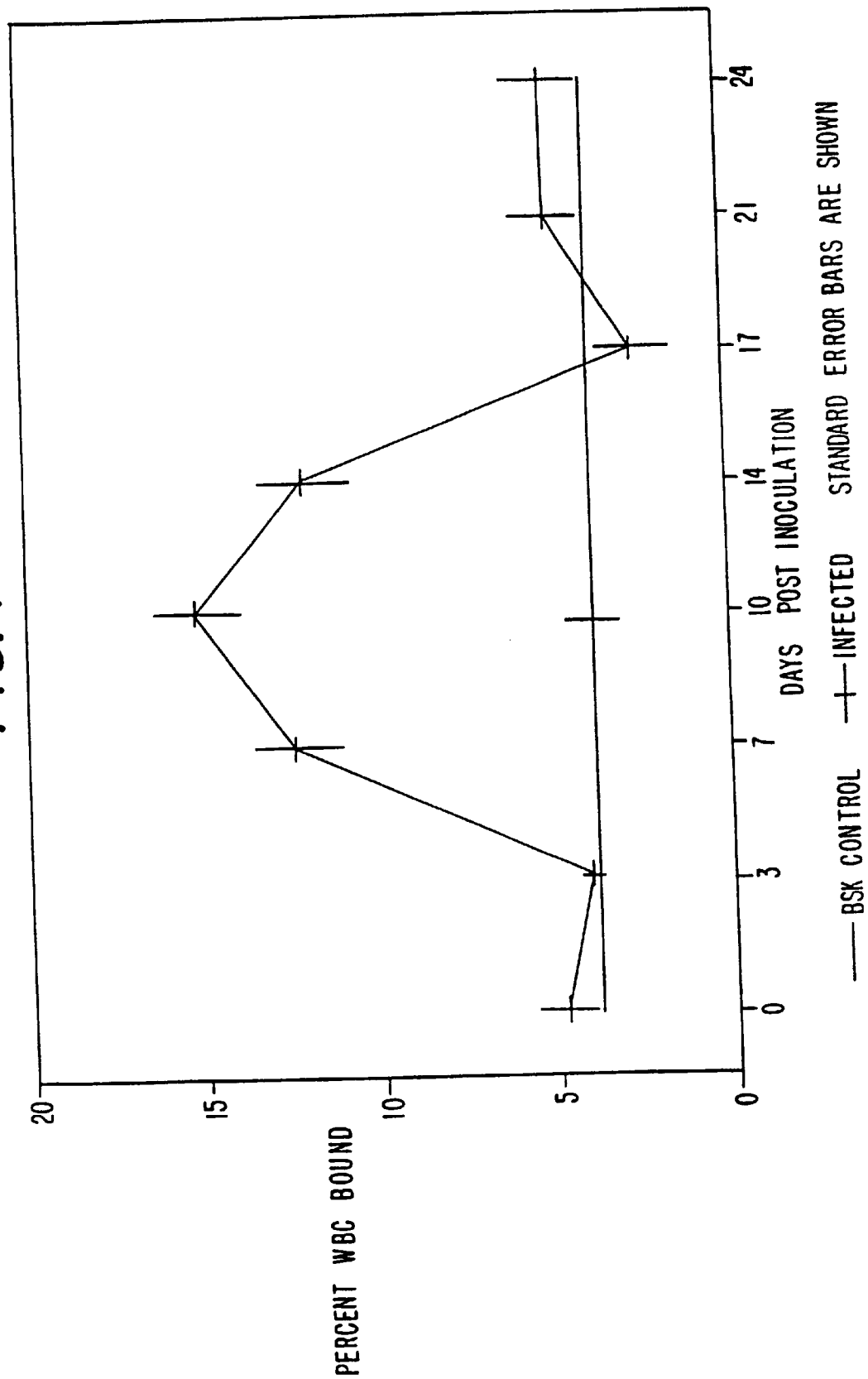
FIG. 4 is a graphical representation of the percentage of white blood cells from mice injected with one of strains N-40, 2684 or 25550 of B.burgdorferi binding B. burgdorferi spirochetes of strain 2684.
Figure 5:
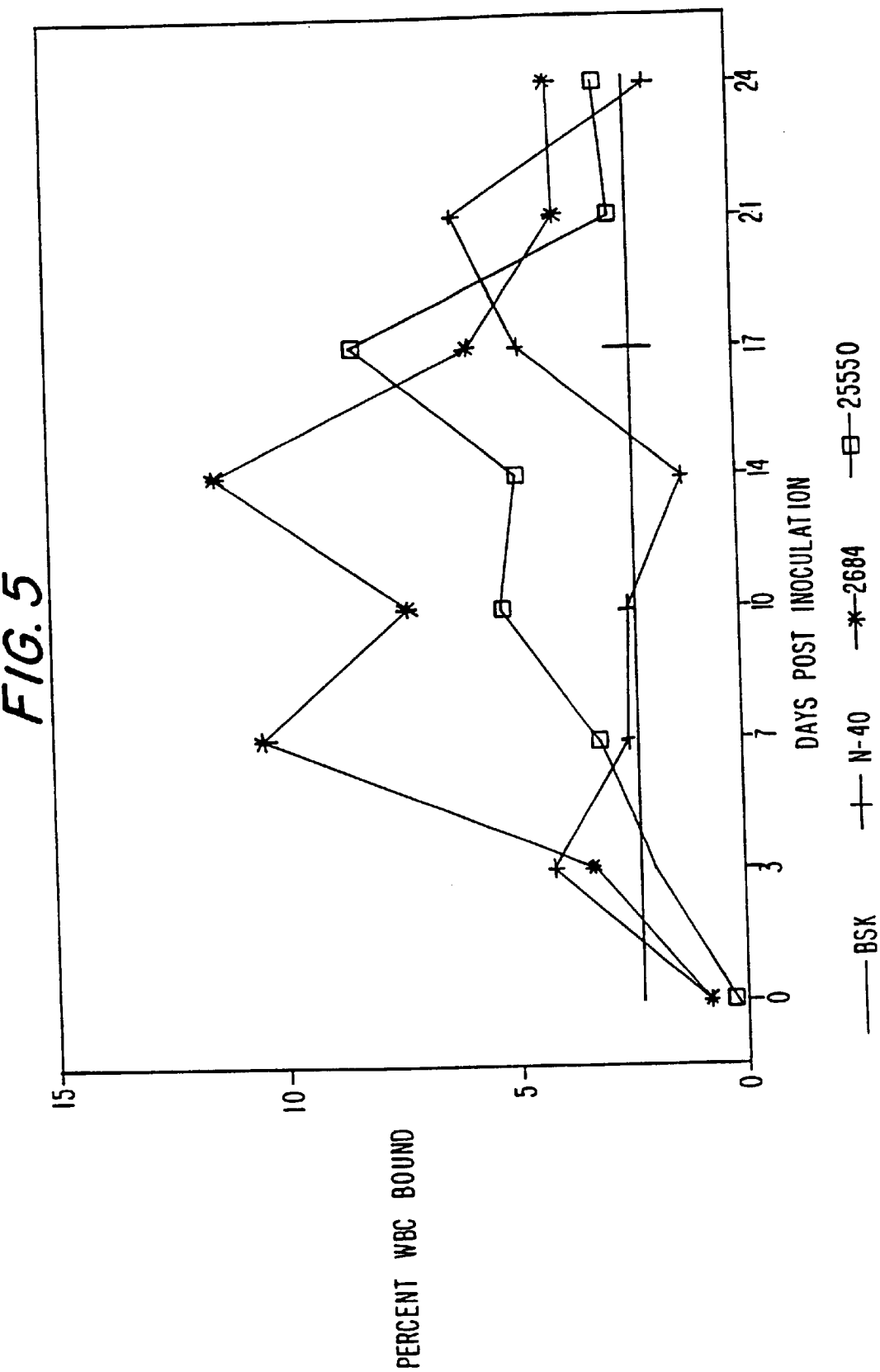
FIG. 5 is a graphical representation of the percentage of white blood cells from mice injected with strain N-40 of B. burgdorferi binding B. burgdorferi spirochetes of strain 25550; the percentage of white blood cells from mice injected with strain 2684 of B. burgdorferi binding B. burgdorferi spirochetes of strain 25550; and the percentage of white blood cells from mice injected with strain 25550 of B. burgdorferi binding B. burgdorferi spirochetes of strain 25550.

To determine whether infection with different *B. burgdorferi* strains produces a comparable binding response, and whether infected host white blood cells bind different *B. burgdorferi* strains, mice were infected with one of three isolates of *B. burdorferi* (N-40, 2684, or 25550). A control group was innoculated with BSK media. The mice were bled twice weekly for one month. Aliquots of each whole blood sample were incubated with one of the three strains of *B. burgdorferi*. Blood smears were prepared, and the binding properties of the white blood cells for the cultured *B. burgdorferi* spirochetes was quantitated. The binding response was also compared with Western blot analysis. The percentage of neutrophils among the white blood cells in the infected and control mice are shown in FIG. 6. The percentage of white blood cells of mice innoculated with each of the three strains of *B. burgdorferi* bound by each of the strains of cultured *B. burgdorferi* are shown in FIGS. 3, 4 and 5. As shown by these Figures, mice infected with any of the three strains responded. In addition, the different *B. burgdorferi* strains used for incubation show binding differences. The binding effect was significant on day three, peaked seven to ten days post infection, and fell to preinfection levels by Day 14.

Double-blind experiments (to avoid observer bias) have been conducted which show that other organisms do not produce cross reactions with *B. burgdorferi*. None of the injected agents induced the binding of Lyme spirochetes above that of the background. It can thus be asserted that there is no evidence that specificity is compromised by secondary or concomitant infections by other organisms.

The method of the claimed invention is not limited to the detection of Borrelia infection. Responsive cells have been shown to recognize organisms other than Borrelia. For example, active binding of *E. coli* bacteria by cells from mice that were injected with *E. coli* has been observed.

In addition, the cell recognition reaction has been induced with isolated proteins. In one experiment, mice were injected with the lipoprotein OspA which had been cloned and expressed by *E. coli*. OspA is the most abundant outer surface protein of *B. burgdorferi*, which has been the focus of much research as a protective antigen for use in a Lyme disease vaccine, as described in published international patent application number WO 92/14488. Blood drawn from the mice was mixed with living *B. burgdorferi* and examined, and the percentage of white blood cells bound was calculated. The results are shown in FIG. 7. Neutrophils capable of binding the spirochetes were in evidence with kinetics that are very similar to that seen when whole organisms are used. This demonstrates that whole organisms are not required to elicit the response. Thus, it may also be possible to replace live organisms with, e.g., ethanol-killed cultured material, or glycoproteins, lipopolysaccharides or lipoproteins (such as OspA or Osp C from *B. burgdorferi*), or mixtures thereof, isolated from the organism of interest for the in vitro assay. More significantly, it shows that the response can be directed to agents that occur in virtually any form. Thus, the test is useful to detect the presence of bacterial, viral, fungal, protozoan and molecular agents, such as some drugs.

For example, the method of the present invention can be used to rapidly and accurately diagnose human and veterinary diseases in their early stages. Such diseases include bacterial infections, e.g., septicemia; bacterial meningitis; gonorrhea, syphilis and other sexually transmitted diseases; streptococcal infections, including those caused by *S. pneumoniae*, *S. pyogenes*, and *S. mutans*; staphylococcal infections, including those caused by *S. aureus* and *S. epidermidis*; listeriosis in humans and circling disease in cattle (both caused by Listeria spp., primarily *L. monocytogenes*); Hemophilis spp. infections, including those caused by *H. influenzae, H. parainfluenzae, H. aphrophilis, H. aegyptius, H. ducreyi* and *H. somnus*; relapsing fever; treponematoses, including bejel, yaws and pinta; leptospirosis; mycoplasmal infections, including those caused by *Mycoplasma pneumoniae*; and chlamydia infections, including those caused by *Chlamydia psittaci* and *C. trachomatis*.

Such diseases also include yeast or fungal infections, e.g. candidiasis, blastomycosis and histoplasmosis, as well as viral infections, e.g. those caused by herpesviruses or papovaviruses such as papilloma.

The method of the present invention is also useful for detecting the presence of, or exposure to, protozoal infections, e.g., those caused by trichomonads and opalinids, as well as infections by parasitic worms such as ascarides, cestodes, Filarioidea, amblystomes and roundworms.

The method of the claimed invention includes the use of any label, and any suitable imaging method, which allows the binding of the foreign substance to the neutrophils to be observed. Preferably the cells are stained with a fluorescent DNA stain, such as Hoechst 33258 or DAPI and viewed under a microscope with an ultraviolet or near-ultraviolet light source. However, other methods are possible, for example, phase contrast microscopy, Nomarski differential contrast microscopy, Hoffman contrast microscopy, darkfield microscopy, interference microscopy or low power scanning or transmission electron microscopy.

It is recognized that the method of the present invention may be automated. For example, an automated digital imaging apparatus could be used with the method of the present invention. The samples are prepared on glass slides which are mounted on the motorized stage of a microscope. The image of the microscopic field is collected by a video camera after automatic focusing. The scanning process proceeds as follows: the camera image is digitized by an analog to digital converter and stored in the memory of the computer. The computer program analyzes the image by searching the characteristic image components. The position of the microscope stage and focusing are saved if any positive elements are found. The computer adjusts the stage and/or focusing for the next field. A complete scan of all of the mounted sample is made by repeating the above process.

The following examples illustrate but do not limit the scope of the invention disclosed in this specification.

EXAMPLES

Example 1

Determination of the Specificity of Binding of Spirochetes of Three Strains of *Borrelia burgdorferi* to the White Blood Cells of Mice This experiment was conducted in order to determine the specificity of binding of spirochetes of three strains of *B. burgdorferi* to the white blood cells of mice inoculated with one of those strains. Five to seven week old female Balb/C mice were used (Jackson Laboratories, Bar Harbor, Me.). There were four inoculation groups: Strains 2684, N-40 and 25550, and a BSK media control. Cultures of the three strains were started from frozen cultures. Cultures were counted on a Petroff-Hauser Chamber the morning of inoculation. Strain N-40 was passage 3, 90% motile, and at a concentration of $7.1 \times 10^7$ spirochetes/ml. Strain 2684 was passage 3, 90% motile, and at a concentration of $6.0 \times 10^7$ spirochetes/ml. Strain 25550 was passage 4, 70% motile, and at a concentration of $3.0 \times 10^7$ spirochetes/ml. *B. burgdorferi* cultures were grown in BSK media at 33–34° C.

Prior to inoculation, the mice were anesthetized with methoxyflurane (Pitman-Moore) and the lower left quadrant of the abdomen was shaved and sterilized with Betadine followed by 95% ethanol. The mice were then inoculated intraperitoneally using a 27 gauge tuberculin syringe with 0.1 to 0.3 ml inoculum under sterile conditions. The mice were carefully observed for several hours following inoculation for after effects of the anesthesia and inoculation.

Each group consisted of 28 mice; 3 mice were euthanized on each of days 0, 3, 7, 10, 14, 17, 21, 24 and 28. The remaining mouse was euthanized on day 36. Sampling of the mice was done on the day of inoculation and every three to four days following the inoculation. At each sampling date, three mice were euthanized for each treatment group. Whole blood from two of these mice was used for the test, and serum was saved from the third for Western blots (Example 2). The mouse was deeply anesthetized with methoxyflurane, decapitated using surgical scissors, and the blood collected using a funnel into a small beaker to which a drop of heparinized saline had been added. The blood was aliquotted into 1.0 ml round bottomed Nunc Cryotubules (USA Scientific, Ocala, Fla.).

Cultures were counted immediately prior to incubation. Incubations were done with each of the three strains. Spirochete concentrations of strain N-40 ranged from approximately 2 to $6 \times 10^7$ spirochetes/ml, and were all passage 3. Strain 2684 had spirochete concentrations ranging from 2.5 to $4.5 \times 10^7$ spirochetes/ml. All cultures were passage 4. Strain 25550 had spirochete concentrations ranging from 1.0 to $6.1 \times 10^7$ spirochetes/ml, and were either passage 4 or 5. For incubating, 100 µl of blood was mixed with 200 µl of culture. The *B. burgdorferi* culture was added to the tubes, the tubes were capped, and placed on a Coulter blood mixer for 30 minutes with rocking. Tubes were checked periodically for proper mixing. At the end of 30 minutes, the tubes were removed, and 4–6 blood smears were made from each onto Corning Single-Frosted microslides (Corning, N.Y.) which had soaked overnight in distilled water, been rinsed at least 1 hour in 50% ethanol, and wiped several times with cheesecloth. The smears were fixed in 95% ethanol for 15 minutes within 3 days. One slide from each group of 4–6 was selected for staining.

Staining was done immediately prior to reading. Slides were soaked 5–15 minutes in 1× phosphate buffered saline (PBS). At the end of this time, the PBS was removed, and concentrated Hoechst's stain was added to it, for a final concentration of 5 µg/ml. Slides were placed in the dark for 30 minutes. At the end of this time, the slides were removed from the staining solution and were immediately covered with a coverglass and sealed with either clear nail polish, rubber cement or mounting media.

Slides were observed under 40×, 60× or 100× on a Ziess Axioplot epifluorescence microscope, an Olympus AH-2 epifluorescence microscope or an Olympus BX-60 epifluorescence microscope. The entire smear was observed. The total numbers of lymphocytes and neutrophils were counted, as well as the number of spirochetes bound to each cell (1–3 or >3).

Data were entered into a spreadsheet program, and the percentage of neutrophils bound with more than three spirochetes of the total number of neutrophils and the total number of cells, the percentage of neutrophils bounds with one or more spirochetes of the total number of neutrophils and the total number of cells, and the percentage of white blood cells bound with one or more spirochetes were calculated. Values from the two mice from each sampling date and each treatment group were averaged, and the standard error was calculated. In cases where the standard error was large, a second slide from each of the two mice was read, for a total of four slides from the group. If values from one slide were vastly different from the other slides, the data from that slide were discarded and the data from the other three slides were averaged.

Because the mice inoculated with BSK provided a baseline for non-specific binding, the values for these mice were averaged over the course of each experiment, and one standard error was calculated. In the first experiment, standard errors indicated that data for each of the three treatment groups (i.e., mice incoulated with strains 2684, N-40 and 25550) were similar enough to justify the combining of this data, and calculating one standard error for each sampling date. This was done for the N-40 (FIG. 3) and 2684 (FIG. 4) incubations, but not for the 25550 incubation (FIG. 5).

Example 2

Western Blot Analysis of the Development of Antibodies

Western blot analysis was utilized to determine the development of antibodies to specific *B. burgdorferi* proteins in the mice.

Sodium dodecyl sulfate polyacrylamide gel electrophoresis (SDS-PAGE) was performed on *B. burgdorferi* tick isolates using a modification of the method described by Laemmli (Laemmli SE 600 vertical slab gel electrophoresis unit, Hoefer Scientific, San Francisco, Calif.). Spirochetes were prepared by washing 150 ml of whole cells from log phase cultures of *B. burgdorferi* three times by centrifugation at 10,000×g for 15 minutes in a 0.1% solution of merthiolate and 1× PBS. The cells were resuspended and the protein concentration was determined using the methods of Bradford (Bradford, 1976).

Approximately 300 μg of *B. burgdorferi*, *L. biflexa*, *T. bryantii* and *E. coli* protein was mixed with SDS sample buffer (187 μl) (0.25 mol/L Tris-HCl, 40% glycerol, 2% sodium dodecyl sulfate (SDS), 20% 2-mercaptoethanol, 0.025% bromophenol blue) and denatured by boiling for 5 minutes. Electrophoresis of the proteins and molecular weight standards (prepared according to the manufacturer, Bio-Rad, Richmond, Calif.) was performed using 11% resolving gels and 4% stacking gels. Electrophoresis was done at a constant current of 100 mA until the dye-front reached 1 cm from the bottom of the gel. Proteins were pre-equilibrated in transfer buffer (25 mM Tris base, 38 mM glycine, 20% methanol, pH 8.3), for 30 minutes, then transferred onto 0.45 μm nitrocellulose membranes as previously described by Towbin et al. (Towbin et al., 1979).

Following transfer, nitrocellulose membranes were stained in Ponceau's stain (Sigma, St. Louis, Mo.) for approximately 10 minutes to determine if proteins were properly transferred. The membranes were cut into strips, placed in a small tray and blocked with 2% Bovine Serum Albumin Fraction IV (BSA) and 1% horse serum in Tris buffered saline for one hour at room temperature with rocking. Strips were rinsed (three 10 minute washes) in was buffer (150 mM NaCl, 10 mM Tris, 0.05% Tween™ 20), overlaid with experimental calf sera (diluted 1:100) and incubated as before for two hours. Serum was removed, strips were washed as described and goat anti-mouse heavy and light chain IgG phosphatase labeled conjugate (Kirkegaard & Perry, Gaithersburg, Md.) (diluted 1:500) was added and incubated for one hour. The strips were rinsed as before and reacted with BCIP/NBT (phosphatase substrate) (Kirkegaard & Perry, Gaithersburg, Md.) until optimal protein band development was achieved (1–10 minutes). The reaction was stopped by the removal of the substrate and rinsing the strips several times with distilled water.

To determine the molecular weights of the protein subunits that reacted with the calf sera, a calibration curve of the relative mobility (Rf) values of the proteins standards was plotted against their molecular weights. Rf values were determined by dividing the distance of the protein migration by the distance of the tracking dye migration. Once the Rf values of the unknown proteins were determined their molecular weight could be estimated from the standard curve.

Example 3

Determination of the Specificity of *Borrelia burgdorferi* Binding to White Blood Cells of Mice Injected with Other Agents This experiment was conducted to determine the specificity of the test. Due to the large number of treatment groups, the experiment was done in several parts. All mice were Balb/C mice (Jackson Laboratories, Bar Harbor, Me.), except where noted.

Treatments and dosages were as follows:

1. Canine Parvovirus MLV (Solvay, Lot # 83000, 1/10 dog dose=0.1 ml)
2. Equine Herpesvirus (Rhinopneumonitis-MLV) (0.1 ml; 1/20 equine dose=0.05 ml)
3. Canine distemper MLV (Solvay, Lot # 81000A, 0.1 ml, 1/10 dog dose)
4. Coagulase negative Staphylococcus spp. (cow skin isolate) (0.3 ml of $1.5\times10^8$ CFU/ml)
5. *B. burgdorferi* N-40 inoculation of C57BL/6J mice (from Jackson Laboratories, Bar Harbor, Me.) ($2.07\times10^6$ spirochetes/mouse)
6. BSK control (0.3 ml)
7. *B. burgdorferi* N-40 control ($1.6\times10^7$ spirochetes/mouse)
8. *E. coli* ($1.0\times10^4$ CFU/mouse)
9. *B. burgdorferi* OspA vaccine (Connaught) (5 μg/mouse in PBS)
10. *Leptospira biflexa* serotype PATOC ($1.4\times10^6$ spirochetes/mouse; culture 90% dead)
11. *Treponema bryantii* ($8\times10^7$ spirochetes/mouse; culture 95% dead)
12. BSK control
13. *B. burgdorferi* N-40 control
14. Mouse Adapted Influenza A/Shanghai/16/89 (Connaught)
15. *L. biflexa* serotype PATOC
16. *T. bryantii*

Counts were done of cultures the morning of inoculation. Syringes for treatments 1–9 were loaded 30 to 120 minutes prior to inoculation. Syringes for treatments 10 and 11 were loaded immediately prior to inoculation. The mice were anesthetized and inoculated as described in Example 1.

There were 15 mice for each treatment group. Three mice were euthanized by guillotine for each of days 0, 3, 7, 10 and 14, and blood collected, as described in Example 1.

Incubations were done with each of the three strains of *B. burgdorferi* (N-40, 2684 and 25550). Cultures were counted immediately prior to incubation. Spirochete concentrations of strain N-40 ranged from 1.5 to $3.5\times10^7$ spirochetes/ml and were passages 4 to 7. Strain 2684 had 1 to $3\times10^7$ spirochetes/ml and were passages 3 to 9. Strain 25550 had 0.75 to $2.5\times10^7$ spirochetes/ml, and were passages 4 to 6. For incubating, 150 μl of blood was mixed with 150 μl of culture. Smears were made and slides were fixed as described in Example 1.

In addition to incubations with *B. burgdorferi*, incubations were also done on selected mice with *E. coli* and Staphylococcus. These incubations were all done on blood from day 10 mice. *E. coli* strain K-12 was incubated with blood from mice inoculated with BSK, N-40 and *E. coli*. Seventy-five μl *E. coli* (concentration $5\times10^8$ CFU/ml) was incubated with 150 μl blood. Staphylococcus was incubated with blood from mice inoculated with Staphylococcus. Fifteen μl of culture (concentration $1\times10^8$ CFU/ml) were incubated with 150 μl blood.

Example 4

Binding of *B. burgdorferi* Spirochetes by White Blood Cells of Mice Inoculated with OspA Protein Balb/C mice in three groups were inoculated according to the method described in Example 1. The first group was inoculated with OspA (Connaught), the second group with Staphylococcus spp., and the third (control) group with BSK medium.

Mice were euthanized, and blood collected, at days 0, 3, 7, 10 and 14 as described in Example 1.

Incubations were done with *B. burgdorferi* of the N-40 strain. Smears were made and the slides were fixed as described in Example 1. The slides were observed under an epifluorescence microscope, and the percentage of white blood cells bound in each inoculation group was calculated. The results are shown in FIG. 7. The dashed portion of the graph of OspA represents disagreement between the samples, so that the values for those points are not established.

Example 5

Determination of the Specificity of Binding of OspA-L and OspA-NL Modified Dynabeads to the Blood of Animals Dynal Dynabeads were prepared by washing three sets of beads from 250 ul aliquots of product (e.g. $10^8$ beads) in several washes of PBS in a 1.5 ml tube. The large magnet was used to remove the fines and solutions and the beads were suspended in 750 ul of PBS. These beads met the following conditions: (1) the beads could be coated with approximately 5 ug protein/$10^7$ beads; (2) the concentration was approximately $10^8$ beads/ml; and (3)the approximate concentration for intended use was 4 beads/cell or more for the reaction. Three groups of beads were prepared in this manner.

Anti-Borrelia antibody was prepared from a serum pool of goats immunized to whole cells of *B. burgdorferi* (Kirkegaard & Perry Laboratories, 2 Cessna Court Gaithersburg, Md., catalog no. 01-97-91) was suspended in a 50% glycerol solution at 1 mg/ml. A 50 ul aliquot was added to the dynabeads, and the tube was gently agitated at room temperature for 20 minutes. BSA was added to a final concentration of 0.1%, and the tube was gently agitated overnight at 37° C. The BSA is recommended to properly "position" the antibody complex on the dynabeads. The beads were washed with PBS with 0.1% BSA using a magnet to remove the antibody solution, and the beads were suspended in a Tris-HCl buffer, and incubated for 24 hours at 37° C. The last step serves to block any remaining groups on the beads, and washes off proteins which are not covalently bound to the beads. Failure to effectively block the beads results in non-specific interactions with other groups on cells with which they can form bonds, such as any free amine, thereby effectively reducing the specificity of the beads to zero.

The second and third group of beads were coated with either OspA-L (lipidated) or OspA-NL (non-lipidated). The OspA-NL was used at a initial concentration of 700 ug/ml, and a total volume of 70 ul was added to the beads; OspA-L was used at an initial concentration of 1210 ug/ml, and a total volume of 50 ul was added to the beads. Both solutions were gently agitated at 37° C. for 24 hours without the addition of BSA.

In most instances, either 70 ul or 140 ul of blood was collected and treated as if the standard Lyme test was being performed. Where living cells were not added, BSK was substituted. Beads were either added as the mixing was performed, or after the mixing. A maximum of 25 ul of the bead suspension was added to the blood. The beads were suspended by Vortex mixing before pipetting into the blood sample. All manipulations of the samples were subsequently performed at 4° C. The samples were washed with PBS with 0.1% BSA with gentle agitation for several minutes. The microfuge tubes were mounted in a carrier, and a magnetic wand was used to separate the beads and the bound cells to the side of the tubes. The fluid could be removed with a pasteur pipet. Washing was performed several times in order to ensure that samples contained no unbound (or only bound) cellular material.

The samples were placed in cytobuckets. These are three well assemblies which allow one to centrifuge the entire contents of a microfuge tube onto a 22 $mm^2$ surface. The experimental and control samples were prepared on the same slide, so that variations in staining that can occur between slides could be controlled. The buckets were spun at very low rates, and the resulting surface had cells evenly spread over it, wherein the bound beads are visible, and the nuclei could be seen in phase contrast. The slides were air dried and fixed in methanol for storage. This method is compatible with the use of aqueous Wright's stain, and it also removes the petroleum sealant used in the cytobucket assembly.

Blood was collected retroorbitally from two (2) animals (mice, as in the previous examples) which had been infected for ten days (see Example 3; $10^6$ organisms, N-40 strain of *B. burgdorferi*) was prepared as described hereinabove, and the samples were photographed using DIC after making drop preparations. No cellular material was found in the controls (media controls), while OspA-L and OspA-NL coated beads exhibited strong binding; platelets were very actively crosslinked into mats of beads. In the samples containing both organisms and anti-Borrelia linked beads, spirochetes and beads were added at the same time. Thus, the binding sequence may have been first to the beads, and then to the cells or vice versa. Antibody linked beads detected cells in infected animals which were not neutrophils, and may be useful in monitoring the entire seroconversion cycle.

This experiment was repeated using blood taken from animals (mice, as in the previous examples) sacrificed at seven days post inoculation by the guillotine method. When spirochetes were added to the cells with gentle agitation, followed by the addition of Anti-Borrelia coated beads, a cell population of neutrophils was isolated which contained virtually none of these cell types in the controls. Other cell types were found in these preparations when fluorescence was used to evaluate the slides. Co-addition of beads and bacteria to the blood created a more severe background. It is likely that the use of BSK, which contains BSA, is a complicating factor in these experiments, and in all of the reactions which follow. Apparently, as the immune response rises, cells which recognize the BSA used in the blocking reactions become available.

Example 6

Determination of the Specificity of Binding of Various Pathogens to the Neutrophils of Animals Ten animals (mice, as per the previous examples) were divided into five groups of two, and each group was inoculated, 5 ug/mouse, intraperitoneally, with one of: Pneumococcal surface protein A (PspA) lipidated, PspA non-lipidated, Influenza B/Panama Haemaglutinin, (detergent extracted HA) tetanus toxoid (each generously provided by Connaught Laboratories, Inc.), and a PBS control. The animals were sacrificed on the seventh day following inoculation. WBC were analyzed by the method outlined in Example 1. Dynabeads were coated with each of the aforementioned antigens and mixed with subject blood. Large cells were plentiful in the blood of the experimental animals, but absent or virtually absent from all control samples. That is, antigen-coated beads bound white blood cells from animals inoculated with the same antigen. Binding was virtually absent from blood of control animals. That these were the same type of neutrophils seen in the Lyme disease test was evident from an examination of the positive controls (blood from Lyme infected mice were incubated with Borrelia and the cells were identified with anti-Borrelia coated beads using the same technical protocol). Both whole blood and whole blood with platelets removed were utilized. In some cases the results were equally specific between these materials. When OspA-L coated beads (as in Example 5) were added to platelet-depleted blood samples from the antigen-inoculated mice, there was no cross-reaction with any of the experimental or control materials. There was also no reaction to positive controls. If platelets were not removed, massive platelet binding was seen with blood from Lyme, HA and PspA materials. Tetanus toxoid provided a positive response, but it was not easily differentiated from the control samples. This may indicate that the protein is less effective in invoking a cell binding response, that the protein was not well bound to the beads, or that the protein was largely degraded. Unlabeled PspA bound cells from both control and experimental animals, and thus, its specificity was marginal.

Example 7

Determination of Potential Cross-Reaction Between Infectious Agents and *Borrelia burgforferi* (Bb) in Lyme Test (ELT)

Groups of mice (as in the previous examples) were inoculated intraperitoneally with one of: *Staphylococcus aureus* ($0.45 \times 10^8$ pfu/mouse), *E. coli* ($1.0 \times 10^4$ pfu/mouse), Treponema ($9.0 \times 10^6$ pfu/mouse), Leptospira ($5 \times 10^6$ pfu/mouse), Influenza virus ($10^6$ organisms/mouse), Parvovirus ($10^6$ organisms/mouse), Herpesvirus ($10^6$ organisms/mouse), Paramyxovirus (Canine distemper; $10^6$ organisms/mouse) and BSK (control). Mice (two of each group) were guillotine bled at 0, 3, 7, 10 and 14 days post inoculation, and the blood was subjected to the Lyme test (ELT) described in Example 1. The results are presented in FIGS. 8a and 8b. No significant binding of *B. burgdorferi* could be seen when ELT was performed on blood from mice infected with these pathogens.

Example 8

Determination of Applicability of ELT to Other Infectious Agents

Leptospira infected mice (inoculated as in Example 7) were guillotine bled 10 days post inoculation, and the blood was monitored for its reaction with exogenous Leptospira and *B. burgdorferi*. The results are presented in FIG. 9, in which the data is presented as a bar graph of the total percentage WBC bound/total WBC (%Cb), and % neutrophils binding>3 Bb/total WBC (%Nb>3). It was found that binding occurs between the white blood cells and exogenous Leptospira, but not between white blood cells and exogenous *B. burgdorferi*. These results indicated that the ELT may be useful for other spirochetes.

Example 9

Evaluation of Alternate Forms of Test Reagents for Cell Binding

Whole *B. burgdorferi* killed by fixation in formalin or merthiolate, washed in saline buffer, was used in ELT as described in Example 1. It was found that this form of *B. burgdorferi* performed equally well in comparison to live *B. burgdorferi* in ELT. However, *B. burgdorferi* killed by freeze/thaw cycles became fractionated and did not perform well in ELT. Hence, the ELT binding response does not require live exogenous Borrelia.

Example 10

Determination of the Presence of Sexual Dimorphism in the Expression of Cell Binding ELT was performed on a total of twelve 7 month old male mice inoculated intraperitoneally with *B. burgdorferi* or BSK (control) (six mice each), and were guillotine bled, two mice per day (one infected, one control) at 0, 3, 7, 14, 21 and 28 days post inoculation. The results are presented in FIG. 10. It was found that the ELT of male mice infected with *B. burgdorferi* was similar to the response found in females.

Example 11

Determination of the Effect of Intradermal Infection Versus Intraperitoneal Infection on ELT Response Mice (as in the previous examples) were inoculated intradermally with *B. burgdorferi* ($10^3$ organisms) and bled, two mice per day (infected) at: 0, 3, 7, 10, 14, 17 and 21 days post inoculation, and the response in ELT and immunoblot was determined. The results are presented in FIGS. 11a and 11b. ELT binding response was strong and serological response (as measured by Western blot) was delayed and very weak. These results show that the ELT binding reponse is separate from measurable antibody response.

Example 12

Determination of the Effect of Platelet Binding of *B. burgdorferi* on ELT Results Since increased platelet clumping and higher background binding occurred when *Borrelia burgdorferi* infected mice were serially retroorbitally bled over a prolonged period, an experiment was designed to directly compare ELT between *B. burgdorferi* infected mice which were either serially bled retroorbitally, or decapitated on similar days after infection, and white blood cell and platelet counts were also performed. The results are shown in FIGS. 12a and 12b. The typical ELT binding response is seen in decapitated mice, and a subdued response is seen in retroorbitally bled mice. Close examination of ELT smears revealed excessive masses of platelets with bound *B. burgdorferi*, and occasional neutrophils in the group infected with *B. burgdorferi* and bled retroorbitally. Mice infected with *B. burgdorferi* but bled by decapitation showed a low level of platelet clumping. Control mice (media inoculated) showed essentially no platelet clumping whether retroorbitally or guillotine bled. WBC differential and reticulocyte numbers were similar among experimental and control groups. A slight increase in platelet clumping was observed in *B. burgdorferi* infected, retroorbitally bled mice. *B. burgdorferi* infection plus repetitive vascular trauma may activate platelets, which then bind the exogenous *B. burgdorferi* added to whole blood in the ELT. *B. burgdorferi* bound to platelets are prevented from binding to neutrophils, resulting in inhibition of the WBC binding response.

Example 13

Determination of ELT in Human Subjects

Figure 13:
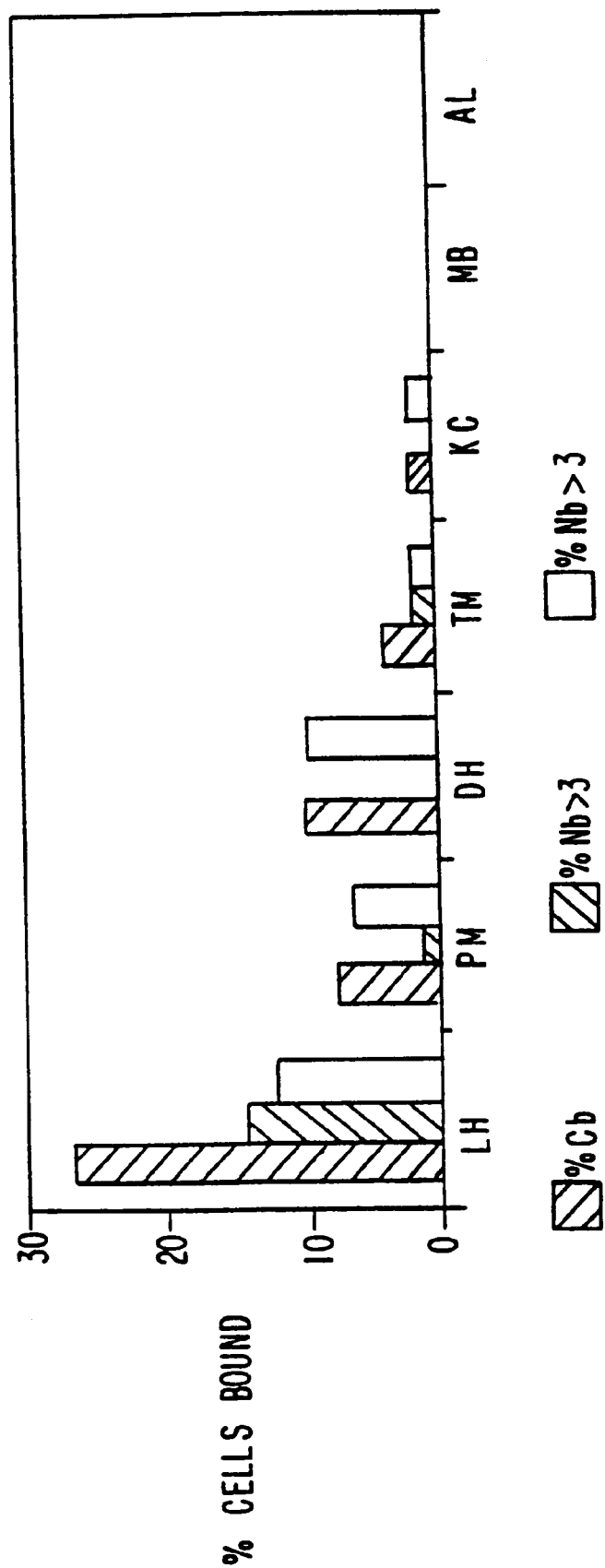
FIG. 13 is a graphical representation of the percentage of cells bound in human volunteers naturally and not (controls) exposed to B. burgdorferi.

Human volunteers with variable exposure to *B. burgdorferi* were tested with ELT and Western blot (as in Example 1). The results are presented in FIG. 13. The patient histories and results are as follows:

LH, 4 year history of chronic Lyme disease, Bell's palsy, arthritis, strong positive western blot, on antibiotic therapy at time of sampling; ELT: strong binding response in all 3 categories;

PM: previously treated for Lyme disease, equivocal western blot, at time of sample, relapse of symptoms; ELT: moderate binding response in %Cb and Nb<3 categories;

DH: Lyme disease symptoms for approximately 1 month, treated for 10 days with amoxicillin, symptoms returned after cessation of antibiotic; western blot: 41 kDa response only; ELT: moderate binding response, consisting of only NB<3;

TM: no history of lyme disease, works in laboratory with *B. burgdorferi*; ELT: minimal binding response;

KC: no history of Lyme disease, no contact with *B. burgdorferi*; ELT: no binding;

AL: no history of Lyme disease, no contact with *B. burgdorferi*; ELT: no binding.

MB: no history of Lyme disease, no contact with *B. burgdorferi*; ELT: no binding.

Data is represented as a bar graph of total %WBC bound/total WBC (%Cb), % Neutrophils binding>3 *B. burgdorferi*/total WBC (%Nb>3), and %Neutrophils binding 1–3 *B. burgdorferi*/total WBC (%Nb<3).

Having thus described in detail certain preferred embodiments of the present invention, it is to be understood that the invention defined by the appended claims is not to be limited by particular deteails set forth in the above description, as many apparent variations thereof are possible without departing from the spirit or scope thereof.

REFERENCES

1. Magnarelli, L. A., et al. 1988. Ticks and Biting Insects Infected with the Etiologic Agent of Lyme Disease, *Borrelia burgdorferi*. J. Clin. Microbiol. 26:1482–1486.

2. Steer, A. C., et al. 1983. The Early Clinical Manifestations of Lyme Disease. Ann. Intern. Med. 99:76–82.

3. Johnston, Y. E., et al. 1985. Lyme Arthritis: Spirochetes Found in Synovial Microangiopathic Lesions. Am. J. Pathol. 118:26–34.

4. Snydman, D. R., et al. 1986. *Borrelia burgdorferi* in Joint Fluid in Chronic Lyme Arthritis. Ann. Intern. Med. 104:798–800.

5. Rawlings, J. A., et al. 1987. Isolation of Borrelia Spirochetes from Patients in Texas. J. Clin. Microbiol. 25:1148–1150.

6. Burgess, E. C., et al. 1988. *Borrelia burgdorferi* Infection in Wisconsin Horses and Cows. Ann. N.Y. Acad. Sci. 539:235–243.

7. Schwan, T. G., et al. 1988. The Urinary Bladder, a Consistent Source of *Borrelia burgdorferi* in Experimentally Infected White-Footed Mice (*Peromyscus leucopus*). J. Clin. Microbiol. 26:893–895.

8. Bosler, E. M., et al. 1987. The prevalence and significance of *Borrelia burgdorferi* in the urine of feral reservoir animals. Zbl. Bakt. Hyg. A263:427–434.

9. Pachner, A. R. 1988. *Borrelia burgdorferi* in the Nervous System: The New "Great Imitator". Ann. N.Y. Acad. Sci. 539:56–64.

10. Golightly, M., et al. 1990. The Laboratory Diagnosis of Lyme Borreliosis. Lab. Med. 21:299–304.

11. Nadelman, R. B., et al. 1990. Isolation of *Borrelia burgdorferi* from the blood of seven patients with Lyme disease. Am. J. Med. 88:21–26.

12. Magnarelli, L. A. 1988. Serologic Diagnosis of Lyme Disease. Ann. N.Y. Acad. Sci. 539:154–161.

13. Shrestha, M. et al. 1985. Diagnosing Early Lyme Disease. Am. J. Med. 78:235–240.

14. Dattwyler, R. J., et al. 1988. Seronegative Lyme Disease: Dissociation of Specific T- and B-Lymphocyte Responses to *Borrelia burgdorferi*. N. Engl. J. Med. 319:1441–1446.

15. Stich-Groh, V., et al. 1988. Possible Pitfalls of an Indirect Immunofluorescence Assay as the Sole Serological Test in the Diagnosis of Lyme Disease. Eurl J. Clin. Microbiol. Infect. Dis. 7:84–85.

16. Luger, S., et al. 1990. Serologic tests for Lyme disease: Interlaboratory variability. Arch. Intern. Med. April, 1990.

17. Luft, B. J., et al. 1988. Specificity of Human B-Cell Responses of Immunodominant Antigens of *Borrelia burgdorferi*. Ann. N.Y. Acad. Sci. 539: 398–401.

18. Finn, A. F., et al. 1990. The Immunology of Lyme Borreliosis. Lab. Med. 21:305–309.

19. Habicht, G. S., et al. 1985. Lyme Disease Spirochetes Induce Human and Murine Interleukin-1 Production. J. Immun. 134:3147–3154.

20. Benach, J. L., et al. 1988. Biological Activity of *Borrelia burgdorferi* Antigens. Ann. N.Y. Acad. Sci. 539:115–125.

21. Coleman, J. L., et al. 1987. Isolation of Antigenic Components from the Lyme Disease Spirochete: Their Role in Early Diagnosis. J. Inf. Dis. 155:756–765.

22. Sigal, L. H. 1990. Immunology of Lyme Disease. N.J. Med. 87:567–571.

23. Szczepanski, A., et al. 1988. Interaction between *Borrelia burgdorferi* and Polymorphonuclear Leukocytes: Phagocytosis and the Induction of the Respiratory Burst. Ann. N.Y. Acad. Sci. 539:425–428.

24. Benach, J., et al. 1984. Interactions of Phagocytes with the Lyme Disease Spirochete: Role of the Fc Receptor. J. Inf. Dis. 150:497–507.

25. Banfi, E., et al. 1989. Rapid flow cytometric studies of *Borrelia burgdorferi* phagocytosis by human polymorphonuclear leukocytes. J. Applied Bact. 67:37–45.

26. Peterson, P. K., et al. 1984. Human Phagocyte Interactions with the Lyme Disease Spirochete. Inf. and Immun. 46:608–611.

27. Benach, J. L., et al. 1984. Phagocytic Cell Responses to in vivo and in vitro Exposure to the Lyme Disease Spirochete. Yale J. Biol. Med. 57:599–605.

28. Thomas, J., et al. 1988. Immunoregulatory abnormalities in *Borrelia burgdorferi* infection. Ann. N.Y. Acad. Sci. 539:431–433.

29. Golightly, M., et al. 1988. Modulation of Natural Killer Cell Activity by *Borrelia burgdorferi*. Ann. N.Y. Acad. Sci. 539:103–111.

30. Luft, B. J., et al. 1989. Treatment of Lyme Borreliosis. Rheum. Dis. Clin. N. A. 15:747–755.

31. Luft, B. J., et al. 1989. A Perspective on the Treatment of Lyme Borreliosis. Rev. Inf. Dis. Vol. II, Supp. 6:S1518–S1525.

32. Dattwyler, R., et al. 1986. Cellular immune response in Lyme disease: The response to mitogen, live *Borrelia*

*burgdorferi*, NK cell function and lymphocyte subsets. Zbl. Bakt. Hyg. 263:151–159.

33. Persing, D. H., et al. 1990. Detection of *Borrelia burgdorferi* Infection in *Ixodes dammini* Ticks with the Polymerase Chain Reaction. J. Clin. Micro. 28:1734–1738.

34. Schwan, T. G., et al. 1989. Identification of *Borrelia burgdorferi* and *B. hermsii* using DNA Hybridization Probes. J. Clin. Micro. 27:1734–1738.

35. Hall, T., et al. 1990. Direct detection of Lyme disease by digital microscopy, in: Proc. 16th Annual Northeast Bioengineering Conf.:61–63.

36. Simon, M. M., et al. 1991. A mouse model for *Borrelia burgdorferi* infection: Approach to a vaccine against Lyme disease. Imm. Today. 12:11–16.

37. Wallich, R., et al. 1990. The *Borrelia burgdorferi* flagellum-associated 41-kilodalton antigen (flagellin): Molecular cloning, expression and amplification of the gene. Infect. Immun. 58(6):1711–1719.

38. Fikrig, E., et al. 1990. Protection of mice against the Lyme disease agent by immunizing with recombinant OspA. Science 250:4980-[?]

39. Collins, C., et al. 1991. Immunoreactive epitopes on an expressed recombinant flagellar protein of *Borrelia burgdorferi*. Infect. Immun. 59(2):514–520.

40. Schwan, T. G., et al. 1988. Changes in Infectivity and Plasmid Profile of the Lyme Disease Spirochete, *Borrelia burgdorferi* as a Result of *Borrelia burgdorferi* Cultivation. Infect. Immun. 56:1831–1836.

41. Dattwyler, R. J., et al. Specific Immune Responses in Lyme Borreliosis: Characterization of T Cell and B Cell Responses to *Borrelia burgdorferi*. Ann. N.Y. Acad. Sci. 93–100.

What is claimed is:

1. A method for detecting a Borrelia bacteria in a human or animal, comprising the steps of:

obtaining fluid or tissue, said fluid or tissue containing polymorphonuclear leukocytes, from said human or animal;

incubating said fluid or tissue with said Borrelia bacteria or with an antigen of said Borrelia bacteria;

labelling said fluid or tissue with one or more labels which detect binding of said polymorphonuclear leukocytes to said Borrelia bacteria or antigen of said Borrelia bacteria;

determining a degree of binding of the Borrelia bacteria or antigen of said Borrelia bacteria to the polymorphonuclear leukocytes; and correlating the degree of binding to detect said Borrelia bacteria in the human or animal.

2. The method of claim 1 wherein said Borrelia bacteria is *Borrelia hermseii*.

3. The method of claim 1 wherein said Borrelia bacteria is *Borrelia burgdorferi*.

4. The method of claim 1 wherein said pathogen is a lipoprotein.

5. The method of claim 4 wherein said lipoprotein is OspA or OspC of *B. burgdorferi*.

6. The method of claim 1 wherein said fluid or tissue is selected from the group consisting of blood, respiratory secretions, urine, cerebrospinal fluid, exudate from skin lesions or abscesses, exudate from the lacrimal sac, and synovial fluid.

7. The method of claim 6 wherein said fluid or tissue is blood.

8. The method of claim 1 wherein said label is a fluorochrome and said determining is fluorescent microscopy.

9. A method for detecting an infection by a Borrelia bacteria in a human or animal, comprising the steps of:

obtaining fluid or tissue, said fluid or tissue containing polymorphonuclear leukocytes, from said human or animal;

incubating said fluid or tissue with said Borrelia bacteria or an antigen of said Borrelia bacteria;

labelling said fluid or tissue with one or more labels which detect binding of said polymorphonuclear leukocytes to said Borrelia bacteria or the antigen of said Borrelia bacteria; and determining a degree of binding of the Borrelia bacteria or the antigen of said Borrelia bacteria to the polymorphonuclear leukocytes; and correlating the degree of binding to detect said infection by Borrelia bacteria in the human or animal.

10. The method of claim 9 wherein said Borrelia bacteria is *Borrelia hermseii*.

11. The method of claim 9 wherein said Borrelia bacteria is *Borrelia burgdorferi*.

12. The method of claim 9 wherein said pathogen is a lipoprotein.

13. The method of claim 12 wherein said lipoprotein is OspA or OspC of *B. burgdorferi*.

14. The method of claim 9 wherein said fluid or tissue is selected from the group consisting of blood, respiratory secretions, urine, cerebrospinal fluid, exudate from skin lesions or abscesses, exudate from the lacrimal sac, and synovial fluid.

15. The method of claim 14 wherein said fluid or tissue is blood.

16. The method of claim 9 wherein said label is a fluorochrome and said determining is fluorescence microscopy.

17. A method for detecting infection by *Borrelia burgdorferi* in a human or animal, comprising the steps of:

removing an aliquot of fluid or tissue, said fluid or tissue containing polymorphonuclear leukocytes, from said human or animal;

incubating said fluid or tissue with cultured *Borrelia burgdorferi*;

labeling said fluid or tissue with a label which images binding of the polymorphonuclear leukocytes to the *Borrelia burgdorferi*;

determining a degree of binding of the *Borrelia burgdorferi* to the polymorphonuclear leukocytes; and correlating the degree of binding to detect said infection by *Borrelia burgdorferi* in the human or animal.

* * * * *